US012042243B2

(12) United States Patent
Kostrzewski et al.

(10) Patent No.: US 12,042,243 B2
(45) Date of Patent: Jul. 23, 2024

(54) SYSTEMS AND METHODS FOR PERFORMING MINIMALLY INVASIVE SURGERY

(71) Applicant: KB MEDICAL, SA, Audubon, PA (US)

(72) Inventors: Szymon Kostrzewski, Lausanne (CH); Billy Nussbaumer, Preverenges (CH); Jimmy Villard, Ecublens (CH)

(73) Assignee: Globus Medical, Inc, Audubon, PA (US)

( * ) Notice: Subject to any disclaimer, the term of this patent is extended or adjusted under 35 U.S.C. 154(b) by 831 days.

(21) Appl. No.: 17/069,482

(22) Filed: Oct. 13, 2020

(65) Prior Publication Data

US 2021/0038333 A1    Feb. 11, 2021

Related U.S. Application Data

(63) Continuation of application No. 14/744,624, filed on Jun. 19, 2015, now Pat. No. 10,828,120.
(Continued)

(51) Int. Cl.
*A61B 34/00* (2016.01)
*A61B 17/34* (2006.01)
*A61B 34/30* (2016.01)
*A61B 90/11* (2016.01)
*A61M 29/00* (2006.01)
(Continued)

(52) U.S. Cl.
CPC .......... *A61B 34/76* (2016.02); *A61B 17/3421* (2013.01); *A61B 34/30* (2016.02); *A61B 90/11* (2016.02); *A61M 29/00* (2013.01); *A61B 2017/3433* (2013.01);
(Continued)

(58) Field of Classification Search
CPC ........ A61B 34/30; A61B 34/76; A61B 90/11; A61B 2034/107; A61B 2034/2055; A61B 2034/2068; A61B 2034/303; A61M 29/00
See application file for complete search history.

(56) References Cited

U.S. PATENT DOCUMENTS

| 4,150,293 A | 4/1979 | Franke |
| 5,246,010 A | 9/1993 | Gazzara et al. |

(Continued)

FOREIGN PATENT DOCUMENTS

| CN | 101010038 A | 8/2007 |
| CN | 101160104 A | 4/2008 |

(Continued)

*Primary Examiner* — William H Matthews

(57) ABSTRACT

Minimally invasive surgical techniques are used to obtain access to vertebrae while protecting soft tissues in the surrounding area. The dilators may be used to provide a working channel through which the operation is performed. Standard dilators may be used with a robotic surgical system to provide precise guidance of surgical tools. A dilator may be held by the robot and automatically repositioned when the surgeon adjusts a trajectory for performing the surgery. The dilator itself may be used as a surgical instrument guide along with dilator adaptors that adjust the diameter of a portion of the dilator to allow for different sized tools to be guided by the dilator. Alternatively, surgical instrument guides may also be held by the robotic arm such that tools are guided by a surgical instrument guide through the dilator to perform a medical procedure.

10 Claims, 12 Drawing Sheets

Related U.S. Application Data

(60) Provisional application No. 62/014,531, filed on Jun. 19, 2014.

(51) Int. Cl.
*A61B 34/10* (2016.01)
*A61B 34/20* (2016.01)

(52) U.S. Cl.
CPC . *A61B 2034/107* (2016.02); *A61B 2034/2055* (2016.02); *A61B 2034/2068* (2016.02)

(56) References Cited

U.S. PATENT DOCUMENTS

| | | | |
|---|---|---|---|
| 5,598,453 A | 1/1997 | Baba et al. |
| 5,772,594 A | 6/1998 | Barrick |
| 5,987,960 A | 11/1999 | Messner et al. |
| 6,031,888 A | 2/2000 | Ivan et al. |
| 6,144,875 A | 11/2000 | Schweikard et al. |
| 6,203,196 B1 | 3/2001 | Meyer et al. |
| 6,306,126 B1 | 10/2001 | Montezuma |
| 6,314,311 B1 | 11/2001 | Williams et al. |
| 6,320,929 B1 | 11/2001 | Von Der Haar |
| 6,477,400 B1 | 11/2002 | Barrick |
| 6,484,049 B1 | 11/2002 | Seeley et al. |
| 6,487,267 B1 | 11/2002 | Wolter |
| 6,490,475 B1 | 12/2002 | Seeley et al. |
| 6,501,981 B1 | 12/2002 | Schweikard et al. |
| 6,535,756 B1 | 3/2003 | Simon et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,666,579 B2 | 12/2003 | Jensen |
| 6,757,068 B2 | 6/2004 | Foxlin |
| 6,782,287 B2 | 8/2004 | Grzeszczuk et al. |
| 6,856,826 B2 | 2/2005 | Seeley et al. |
| 6,856,827 B2 | 2/2005 | Seeley et al. |
| 6,920,347 B2 | 7/2005 | Simon et al. |
| 6,922,632 B2 | 7/2005 | Foxlin |
| 6,988,009 B2 | 1/2006 | Grimm et al. |
| 6,996,487 B2 | 2/2006 | Jutras et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,301,648 B2 | 11/2007 | Foxlin |
| 7,313,430 B2 | 12/2007 | Urquhart et al. |
| 7,318,805 B2 | 1/2008 | Schweikard et al. |
| 7,324,623 B2 | 1/2008 | Heuscher et al. |
| 7,327,865 B2 | 2/2008 | Fu et al. |
| 7,460,637 B2 | 12/2008 | Clinthorne et al. |
| 7,493,153 B2 | 2/2009 | Ahmed et al. |
| 7,505,617 B2 | 3/2009 | Fu et al. |
| 7,623,902 B2 | 11/2009 | Pacheco |
| 7,643,862 B2 | 1/2010 | Schoenefeld |
| 7,661,881 B2 | 2/2010 | Gregerson et al. |
| 7,683,331 B2 | 3/2010 | Chang |
| 7,683,332 B2 | 3/2010 | Chang |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,725,253 B2 | 5/2010 | Foxlin |
| 7,726,171 B2 | 6/2010 | Langlotz et al. |
| 7,760,849 B2 | 7/2010 | Zhang |
| 7,796,728 B2 | 9/2010 | Bergfjord |
| 7,813,838 B2 | 10/2010 | Sommer |
| 7,835,778 B2 | 11/2010 | Foley et al. |
| 7,835,784 B2 | 11/2010 | Mire et al. |
| 7,840,256 B2 | 11/2010 | Lakin et al. |
| 7,844,320 B2 | 11/2010 | Shahidi |
| 7,853,305 B2 | 12/2010 | Simon et al. |
| 7,853,313 B2 | 12/2010 | Thompson |
| 7,900,524 B2 | 3/2011 | Calloway et al. |
| 7,940,999 B2 | 5/2011 | Liao et al. |
| 7,945,012 B2 | 5/2011 | Ye et al. |
| 7,945,021 B2 | 5/2011 | Shapiro et al. |
| 8,019,045 B2 | 9/2011 | Kato |
| 8,021,310 B2 | 9/2011 | Sanborn et al. |
| 8,052,688 B2 | 11/2011 | Wolf, II |
| 8,086,299 B2 | 12/2011 | Adler et al. |
| 8,098,914 B2 | 1/2012 | Liao et al. |
| 8,100,950 B2 | 1/2012 | St. Clair et al. |
| 8,116,430 B1 | 2/2012 | Shapiro et al. |
| 8,121,249 B2 | 2/2012 | Wang et al. |
| 8,150,494 B2 | 4/2012 | Simon et al. |
| 8,208,708 B2 | 6/2012 | Homan et al. |
| 8,224,024 B2 | 7/2012 | Foxlin et al. |
| 8,311,611 B2 | 11/2012 | Csavoy et al. |
| 8,335,557 B2 | 12/2012 | Maschke |
| 8,358,818 B2 | 1/2013 | Miga et al. |
| 8,379,791 B2 | 2/2013 | Forthmann et al. |
| 8,386,019 B2 | 2/2013 | Camus et al. |
| 8,394,099 B2 | 3/2013 | Patwardhan |
| 8,462,911 B2 | 6/2013 | Vesel et al. |
| 8,526,700 B2 | 9/2013 | Isaacs |
| 8,541,970 B2 | 9/2013 | Nowlin et al. |
| 8,560,118 B2 | 10/2013 | Green et al. |
| 8,597,198 B2 | 12/2013 | Sanborn et al. |
| 8,611,985 B2 | 12/2013 | Lavallee et al. |
| 8,630,389 B2 | 1/2014 | Kato |
| 8,634,897 B2 | 1/2014 | Simon et al. |
| 8,660,635 B2 | 2/2014 | Simon et al. |
| 8,678,647 B2 | 3/2014 | Gregerson et al. |
| 8,696,458 B2 | 4/2014 | Foxlin et al. |
| 8,706,185 B2 | 4/2014 | Foley et al. |
| 8,727,618 B2 | 5/2014 | Maschke et al. |
| 8,738,115 B2 | 5/2014 | Amberg et al. |
| 8,740,882 B2 | 6/2014 | Jun et al. |
| 8,781,186 B2 | 7/2014 | Clements et al. |
| 8,781,630 B2 | 7/2014 | Banks et al. |
| 8,787,520 B2 | 7/2014 | Baba |
| 8,792,704 B2 | 7/2014 | Isaacs |
| 8,798,231 B2 | 8/2014 | Notohara et al. |
| 8,812,077 B2 | 8/2014 | Dempsey |
| 8,814,793 B2 | 8/2014 | Brabrand |
| 8,818,105 B2 | 8/2014 | Myronenko et al. |
| 8,821,511 B2 | 9/2014 | Von Jako et al. |
| 8,867,703 B2 | 10/2014 | Shapiro et al. |
| 8,888,821 B2 | 11/2014 | Rezach et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |

(56) References Cited

U.S. PATENT DOCUMENTS

| | | |
|---|---|---|
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2004/0024311 A1 | 2/2004 | Quaid, III |
| 2004/0076259 A1 | 4/2004 | Jensen et al. |
| 2006/0087274 A1 | 4/2006 | Curtis |
| 2006/0184396 A1 | 8/2006 | Dennis et al. |
| 2006/0291612 A1 | 12/2006 | Nishide et al. |
| 2007/0038059 A1 | 2/2007 | Sheffer et al. |
| 2007/0073133 A1 | 3/2007 | Schoenefeld |
| 2008/0004523 A1 | 1/2008 | Jensen |
| 2008/0013809 A1 | 1/2008 | Zhu et al. |
| 2008/0082109 A1 | 4/2008 | Moll et al. |
| 2008/0108991 A1 | 5/2008 | Von Jako |
| 2008/0144906 A1 | 6/2008 | Allred et al. |
| 2008/0161680 A1 | 7/2008 | Von Jako et al. |
| 2008/0235052 A1 | 9/2008 | Node-Langlois et al. |
| 2008/0269596 A1 | 10/2008 | Revie et al. |
| 2008/0287781 A1 | 11/2008 | Revie et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0149857 A1* | 6/2009 | Culbert ............... A61B 1/0684 606/191 |
| 2009/0185655 A1 | 7/2009 | Koken et al. |
| 2009/0198121 A1 | 8/2009 | Hoheisel |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0228117 A1 | 9/2010 | Hartmann |
| 2010/0274120 A1 | 10/2010 | Heuscher |
| 2011/0098553 A1 | 4/2011 | Robbins et al. |
| 2011/0282189 A1 | 11/2011 | Graumann |
| 2011/0286573 A1 | 11/2011 | Schretter et al. |
| 2012/0035507 A1 | 2/2012 | George et al. |
| 2012/0051498 A1 | 3/2012 | Koishi |
| 2012/0101508 A1 | 4/2012 | Choi et al. |
| 2012/0143084 A1 | 6/2012 | Shoham |
| 2012/0226145 A1 | 9/2012 | Chang et al. |
| 2012/0235909 A1 | 9/2012 | Birkenbach et al. |
| 2012/0294498 A1 | 11/2012 | Popovic |
| 2013/0016889 A1 | 1/2013 | Myronenko et al. |
| 2013/0060146 A1 | 3/2013 | Yang et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0281821 A1 | 10/2013 | Liu et al. |
| 2013/0303883 A1* | 11/2013 | Zehavi ............... A61B 6/5247 600/417 |
| 2013/0307955 A1 | 11/2013 | Deitz et al. |
| 2013/0342578 A1 | 12/2013 | Isaacs |
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | |
|---|---|---|
| CN | 1612038 B | 5/2011 |
| CN | 202146362 U | 2/2012 |
| CN | 102451040 A | 5/2012 |

* cited by examiner

SYSTEMS AND METHODS FOR PERFORMING MINIMALLY INVASIVE SURGERY

CROSS-REFERENCE TO RELATED APPLICATIONS

This Patent Application is a continuation application of U.S. patent application Ser. No. 14/744,624, filed on Jun. 19, 2015 (published as U.S. Pat. Pub. No. 2015-0366624), which is a non-provisional patent application claiming priority to U.S. Provisional Patent Application No. 62/014,531, filed Jun. 19, 2014, the entire contents of all of which are hereby incorporated by reference in their entireties for all purposes.

BACKGROUND OF THE INVENTION

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeon's field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading.

Certain force feedback systems are used by surgeons in certain procedures; however such systems have a large footprint and take up valuable, limited space in the operating room. These systems also require the use of surgical tools that are specially adapted for use with the force feedback system, and the training required by surgeons to operate such systems can be significant. Moreover, surgeons may not be able to use expertise they have developed in performing spinal surgeries when adapting to use of the current force feedback systems. Such systems, while precise, may require more surgical time and more operating room preparation time to ready placement of the equipment for surgery. Thus, there is a need for systems, apparatus, and methods that provide enhanced precision in performing surgeries such as spinal surgeries.

SUMMARY OF THE INVENTION

Described herein are systems, apparatus, and methods for precise placement and guidance of tools during surgery, particularly spinal surgery, using minimally invasive surgical techniques. The system features a portable robot arm with end effector for precise positioning of a surgical tool. Minimally invasive surgical techniques are used to obtain access to vertebrae while protecting soft tissues in the surrounding area. These techniques minimize blood loss, postoperative pain, and scaring while providing for faster recoveries. The disclosed technology utilizes robotic surgical systems with minimally invasive surgical techniques and automated planning to enhance the precision in performing surgeries, such as spinal surgeries.

During minimally invasive surgical procedures, dilators may be used to create a working channel through which an operation is performed. The dilators may be a set of tubes with increasing diameters which are inserted into a small incision one at a time until the desired diameter of the working channel is achieved. The dilators may be used with a robotic surgical system (e.g., attached to the robotic arm) to perform a minimally invasive surgery. This allows the usage, in certain embodiments, of standard dilators and a robotic surgical system to provide precise guidance of surgical tools through a dilator and greater flexibility. The dilator may be held by the robot and automatically repositioned when the surgeon adjusts the trajectory along which, for example, a hole is prepared in a vertebra. Adjustment of the end effector of the robotic surgical system automatically adjusts an angle and/or position of the dilator attached to the robot with respect to the vertebrae and aligns an axis defined by the dilator with a desired trajectory during a surgical procedure without removal of the dilator from the patient tissue during the repositioning.

For example, first dilator may be used to access a vertebrae of a patient through the patient's muscles and skin, thereby defining a working channel for accessing the vertebrae. One or more subsequent dilators may be slid over the first dilator. Each of the one or more subsequent dilators are configured to be positioned over the preceding dilators and increase the size of the working channel. Each dilator except the last added dilator is configured to be removed from the patient thereby leaving the last added dilator. The last added dilator is configured to be attached to an end effector of a robotic arm using a dilator fixator. A manipulator is configured to allow robotically-assisted or unassisted positioning and/or movement of the last added dilator by a user with at least four degrees of freedom to align an axis defined by the last added dilator with respect to the vertebrae. Adjustment of the manipulator automatically adjusts an angle and/or position of the attached dilator with respect to the vertebrae and aligns an axis defined by the attached dilator with a desired trajectory during a surgical procedure without removal of the attached dilator from the patient tissue during the repositioning.

The system requires only minimal training by surgeons/operators, is intuitive to use, and has a small footprint with significantly reduced obstruction of the operating table. The system works with existing, standard surgical tools, does not require increased surgical time or preparatory time, and safely provides the enhanced precision achievable by robotic-assisted systems. Moreover, the system allows for a desired trajectory (e.g., for a drill guide during spinal surgery) to be set in a variety of manners based on the circumstances of the surgery. For example, some surgical procedures are planned pre-operatively with the surgeon defining the desired position of an implant using imaging technology, such as CT images (e.g., 3D CT images). The desired position of the implant may also be determined and proposed by the system. In the operating room the surgeon may be guided by the robotic system (e.g., robotic guidance of the surgical tools) to accurately execute the planning.

A mobile cart houses a robot arm with an end effector that holds various standard surgical tools/implants, such as a drill or screw. Positioning such surgical tools with precision is critical. The robot arm provides more precise, stable placement of such tools than can be achieved manually, where placement is guided, yet intuitive. The mobile cart permits easy set-up and use of the system. Once stabilization is engaged, the mobile cart is secured in place on the operating room floor and cannot move. In certain embodiments, the robot cart houses the robot, robot controller, supervisor interlock system, power system, riding system, and interface to the navigation system.

In one aspect, the disclosed technology includes a method of performing minimally invasive spinal surgery with a robotic surgical system, the method including: maneuvering a first dilator to access a vertebrae of a patient through the patient's muscles and skin, wherein the dilator defines a working channel for accessing the vertebrae; increasing the size of the working channel (e.g., using one or more dilators subsequent to the first dilator, whereby a subsequent dilator is temporarily secured in the patient tissue); attaching the first dilator or the subsequent dilator to the end effector of the robotic arm using a dilator fixator; following attachment of the first or a subsequent dilator to the end effector, repositioning the end effector thereby automatically adjusting an angle and/or position of the attached dilator with respect to the vertebrae and aligning an axis defined by the attached dilator with a desired trajectory during a surgical procedure without removal of the attached dilator from the patient tissue during the repositioning.

In certain embodiments, increasing the size of the working channel includes: maneuvering a second dilator over the first dilator, wherein the second dilator is sized and shaped to slide over the first dilator and increase the size of the working channel; and after positioning the second dilator over the first dilator (and/or after positioning one or more subsequent dilators over the preceding dilators), removing the first dilator (and/or other previous dilators except the final added dilator) from the patient, thereby leaving the last added dilator, wherein the attached dilator is the last added dilator.

In certain embodiments, the attached dilator is the dilator with largest circumference.

In certain embodiments, increasing the size of the working channel includes: expanding the diameter of the first dilator thereby increasing the diameter of the working channel, wherein the dilator attached to the end effector is the first dilator.

In certain embodiments, the method further includes placing a surgical instrument guide at least partially inside of, in front of, or adjacent to the attached dilator, wherein the surgical instrument guide is sized and shaped to fit at least partially inside the attached dilator along an axis defined by said dilator.

In certain embodiments, the end effector includes a surgical instrument guide attached thereto, configured to hold and/or restrict movement of a surgical instrument therethrough.

In certain embodiments, the surgical instrument guide is at least one of a drill bit guide, tap guide, screwdriver guide, screw guide, awl guide, and implant guide.

In certain embodiments, the surgical instrument is at least one of a drill bit, tap, screwdriver, screw, implant, and awl, wherein the surgical instrument is configured to slide through the surgical instrument guide.

In certain embodiments, the attached dilator is configured to hold and/or restrict movement of a surgical instrument therethrough.

In certain embodiments, the method includes registering the patient, wherein registering the patient comprises identifying the transformation between the actual patient anatomy and one or more medical images; maneuvering the end effector towards the vertebrae on which the surgeon will operate; determining, by a processor of a computing device, an ideal implant trajectory; and providing, by the processor, for display on a graphical user interface, the ideal implant trajectory for review by the surgeon, wherein (i) the surgeon may adapt the ideal implant trajectory if needed using hands-on planning, and (ii) the surgeon acknowledges the ideal implant trajectory or the adapted trajectory thereby causing the acknowledged trajectory to be stored as the desired trajectory.

In certain embodiments, the method includes, prior to maneuvering the attached dilator: moving a mobile cart transporting a robotic surgical system comprising a robotic arm in proximity to an operating table, wherein the robotic arm has an end effector; and stabilizing the mobile cart.

In another aspect, the disclosed technology includes a robotic surgical system for performing minimally invasive surgery, the system including: a robotic arm with an end effector; a first dilator to access a vertebrae of a patient through the patient's muscles and skin, wherein the first dilator defines a working channel for accessing the vertebrae; one or more subsequent dilators sized and shaped to slide over the first dilator and/or one or more of the one or more subsequent dilators, wherein: the one or more subsequent dilators comprise a last added dilator, each of the one or more subsequent dilators are configured to be positioned over the preceding dilators and increase the size of the working channel, each dilator except the last added dilator is configured to be removed from the patient thereby leaving the last added dilator, the last added dilator is configured to be attached to the end effector of the robotic arm using a dilator fixator; and a manipulator configured to allow robotically-assisted or unassisted positioning and/or movement of the end effector by a user with at least four degrees of freedom thereby automatically adjusting an angle and/or position of the last added dilator with respect to the vertebrae and aligning an axis defined by the last added dilator with a desired trajectory during a surgical procedure without removal of the last added dilator from the patient tissue during the repositioning.

In certain embodiments, each one or more subsequent dilators have a circumference larger than the circumference of the first dilator, and the one or more subsequent dilators increase the size of the working channel as each subsequent dilator is added.

In certain embodiments, the system includes a surgical instrument guide configured to be placed inside of the attached dilator, wherein the surgical instrument guide is sized and shaped to fit at least partially inside the attached dilator along an axis defined by the dilator.

In certain embodiments, the end effector comprises the surgical instrument guide attached thereto, configured to hold and/or restrict movement of a surgical instrument therethrough.

In certain embodiments, the surgical instrument guide is at least one of a drill bit guide, tap guide, screwdriver guide, screw guide, awl guide, and implant guide.

In certain embodiments, the surgical instrument is at least one of a drill bit, tap, screwdriver, screw, implant, and awl, wherein the surgical instrument is configured to slide through the surgical instrument guide.

In certain embodiments, the attached dilator is the dilator with largest circumference.

In certain embodiments, the attached dilator is configured to hold and/or restrict movement of a surgical instrument therethrough.

In certain embodiments, the system includes a processor; and a memory, the memory storing instructions that, when executed by the processor, cause the processor to: store a transformation between the actual patient anatomy and one or more medical images; determine an ideal implant trajectory; and provide, for display on a graphical user interface, the ideal implant trajectory for review by the surgeon, wherein (i) the surgeon may adapt the ideal implant trajectory if needed using hands-on planning, and (ii) the surgeon acknowledges the ideal implant trajectory or the adapted trajectory thereby causing the acknowledged trajectory to be stored as the desired trajectory.

In another aspect, the disclosed technology includes a robotic surgical system for performing minimally invasive surgery, the system including: a robotic arm with an end effector; a dilator to access a vertebrae of a patient through the patient's muscles and skin, wherein: the dilator defines a working channel for accessing the vertebrae; the dilator is configured to be expanded to increase the size of the working channel, the dilator is configured to be attached to an end effector of a robotic arm using a dilator fixator; and a manipulator configured to allow robotically-assisted or unassisted positioning and/or movement of the end effector by a user with at least four degrees of freedom thereby automatically adjusting an angle and/or position of the dilator with respect to the vertebrae and aligning an axis defined by the dilator with a desired trajectory during a surgical procedure without removal of the dilator from the patient tissue during the repositioning.

In certain embodiments, the system includes a surgical instrument guide configured to be placed inside of the dilator, wherein the surgical instrument guide is sized and shaped to fit at least partially inside the dilator along an axis defined by the dilator.

In certain embodiments, the end effector includes the surgical instrument guide attached thereto, configured to hold and/or restrict movement of a surgical instrument therethrough.

In certain embodiments, the surgical instrument guide is at least one of a drill bit guide, tap guide, screwdriver guide, screw guide, awl guide, and implant guide.

In certain embodiments, the surgical instrument is at least one of a drill bit, tap, screwdriver, screw, implant, and awl, wherein the surgical instrument is configured to slide through the surgical instrument guide.

In certain embodiments, the robotic arm is configured to be maneuvered to a desired position to align an axis defined by the surgical instrument guide at a desired trajectory in relation to the vertebrae, wherein the dilator connected to the end effector of the robotic arm is automatically positioned as the robotic arm is maneuvered to adjust to the desired trajectory;

In certain embodiments, the dilator is configured to hold and/or restrict movement of a surgical instrument therethrough.

In certain embodiments, the system includes a processor; and a memory, the memory storing instructions that, when executed by the processor, cause the processor to: store a transformation between the actual patient anatomy and one or more medical images; determine an ideal implant trajectory; and provide, for display on a graphical user interface, the ideal implant trajectory for review by the surgeon, wherein (i) the surgeon may adapt the ideal implant trajectory if needed using hands-on planning, and (ii) the surgeon acknowledges the ideal implant trajectory or the adapted trajectory thereby causing the acknowledged trajectory to be stored as the desired trajectory.

In another aspect, the disclosed technology includes a robotic surgical system for performing surgery, the system including: a robotic arm comprising a force and/or torque control end-effector, wherein the end-effector comprises a surgical tool holder attached to the robotic arm via a force sensor, wherein the surgical tool holder is sized and shaped to hold a surgical tool; an actuator for controlled movement of the robotic arm and/or positioning of the surgical tool holder; a navigation system for detection of (i) a position of a surgical tool held by the robotic arm and (ii) patient position, the navigation system including: a patient navigation marker associated a patient anatomy for identifying the patient position, a robot navigation marker associated the surgical tool for identifying the surgical tool position, and a tracking camera; a processor and a non-transitory computer readable medium storing instructions thereon, wherein the instructions, when executed, cause the processor to: determine one or more projected trajectories based on a position of a surgical tool according to a tool navigation marker, a patient position according to a patient navigation marker, and one or more patient medical images; provide, for display on a graphical user interface, the one or more projected trajectories; receive a selection of the desired trajectory from the one or more projected trajectories; assist a surgeon in bringing the surgical tool holder to the desired trajectory, wherein assisting the surgeon in bringing the surgical tool holder to the desired trajectory comprises at least one of (i) and (ii): (i) providing attractive haptic feedback (e.g., force and/or torque) to guide the surgeon to bring the surgical tool holder to the target position, and/or (ii) providing resistive haptic feedback (e.g., force and/or torque) to resist movement of the surgical tool holder in directions away from the desired trajectory; and after the surgical tool holder is brought to the desired trajectory, lock the surgical tool holder along the desired trajectory.

In certain embodiments, the instructions, when executed by the processor, cause the processor to, prior to assisting a surgeon in bringing the surgical tool holder to the desired trajectory, detect, via a sensor, the presence of a hand on a handle of the robotic arm.

In certain embodiments, the handle extends at least in part from the robotic arm.

In certain embodiments, the instructions to determine one or more projected trajectories comprises instructions that, when executed by the processor, cause the processor to: receive, from a navigation pointer, identification of a point along the patient anatomy; and determine the one or more projected trajectories based on the identified point along the patient anatomy.

In certain embodiments, receiving a selection of a desired trajectory from the one or more projected trajectories comprises receiving a modified trajectory based at least in part on one of the one or more trajectories, wherein the desired trajectory is the modified trajectory.

In certain embodiments, the instructions, when executed by the processor, cause the processor to, prior to receiving a selection of a desired trajectory from the one or more projected trajectories, render and display a representation of the projected trajectory and at least one of the one or more medical images.

In certain embodiments, the determination of the projected trajectory and the rendering and display of the projected trajectory is updated as the position of the surgical tool holder is changed, thereby providing visual feedback to a user to assist the user in positioning the surgical tool holder at a desired position.

In certain embodiments, the instructions, when executed by the processor, cause the processor to, prior to locking the surgical tool holder along the desired trajectory, detecting, via a force sensor, a collision between the surgical tool holder an another object.

In certain embodiments, the instructions, when executed by the processor, cause the processor to measure movement of the patient position and move the surgical tool holder based on said measured movement.

In certain embodiments, the one or more medical images comprise one or more of an MRI, CT, fluoroscopy, CT (ISO-C-3D) or 3D fluoroscopy medical image.

In certain embodiments, the one or more medical images comprise at least one of a pre-operative or an intra-operative medical image.

In certain embodiments, registering the patient is performed by the robotic surgical system automatically based at least in part on a patient navigation marker attached to the patient anatomy, and the one or more medical images.

In certain embodiments, registering the patient is performed using at least one or manual point-to-point registration, surface matching, and fluoroscopy-based registration.

In certain embodiments, the instructions to provide, for display on a graphical user interface, the one or more projected trajectories comprise instructions to provide a list of trajectories, for display on a graphical user interface, the one or more projected trajectories.

In certain embodiments, the instructions to provide, for display on a graphical user interface, the one or more projected trajectories comprise instructions to provide a preview of at least one of the one or more trajectories with the at least one of the one or more patient medical images.

In certain embodiments, the system includes a mobile cart that permits the robotic surgical system to be moved in and out of the operating room, wherein the mobile cart comprises a plurality of wheels for moving the robotic surgical system and a plurality of rigid legs on which the mobile cart sits to stabilize the robotic surgical system on an operating room floor, wherein either the plurality of wheels or the plurality of rigid legs are retractable.

In certain embodiments, the system includes a handle extending from the end effector that may be grasp by a hand of a user to move and/or position the end effector—with at least four degrees of freedom.

In certain embodiments, force sensor located between the robotic arm and the tool holder for measuring forces and/or torques applied by a user to the first surgical tool held by the tool holder.

In certain embodiments, the system includes a sensor that detects the presence of the hand of the user on the handle.

In certain embodiments, during an operation the end-effector is only moved by the robotic surgical system when the sensor detects the hand of the user on the handle, thereby reducing the likelihood that the end-effector is moved unintentionally.

In another aspect, the disclosed technology includes a method of performing surgery with a robotic surgical system, the method including: determining, by a processor of a computing device, one or more projected trajectories based on a position of a surgical tool holder according to a tool navigation marker, a patient position according to a patient navigation marker, and one or more patient medical images; providing, by the processor, for display on a graphical user interface, the one or more projected trajectories; receiving, by the processor, a selection of the desired trajectory from the one or more projected trajectories; assisting, by the processor, a surgeon in bringing the surgical tool holder to the desired trajectory, wherein assisting the surgeon in bringing the surgical tool holder to the desired trajectory comprises at least one of (i) and (ii): (i) providing attractive haptic feedback (e.g., force and/or torque) to guide the surgeon to bring the surgical tool holder to the target position, and/or (ii) providing resistive haptic feedback (e.g., force and/or torque) to resist movement of the surgical tool holder in directions away from the desired trajectory; and after the surgical tool holder is brought to the desired trajectory, locking, by the processor, the surgical tool holder along the desired trajectory.

In certain embodiments, the method includes, prior to assisting a surgeon in bringing the surgical tool holder to the desired trajectory, detecting, by the processor, via a sensor, the presence of a hand on a handle of the robotic arm.

In certain embodiments, the handle extends at least in part from the robotic arm.

In certain embodiments, the method includes determining one or more projected trajectories includes: receiving, by the processor, from a navigation pointer, identification of a point along the patient anatomy; and determining, by the processor, the one or more projected trajectories based on the identified point along the patient anatomy. wherein a selection of a desired trajectory from the one or more projected trajectories comprises receiving a modified trajectory based at least in part on one of the one or more trajectories, wherein the desired trajectory is the modified trajectory.

In certain embodiments, the method includes registering the patient, wherein registering the patient comprises determining a transformation between a patient anatomy and one or more medical images.

In certain embodiments, the method includes, prior to receiving a selection of a desired trajectory from the one or more projected trajectories, rendering and displaying a representation of the projected trajectory and at least one of the one or more medical images.

In certain embodiments, the determination of the projected trajectory and the rendering and display of the projected trajectory is updated as the position of the surgical tool holder is changed, thereby providing visual feedback to a user to assist the user in positioning the surgical tool holder at a desired position.

In certain embodiments, the method includes, prior to locking the surgical tool holder along the desired trajectory, detecting, via a force sensor, a collision between the surgical tool holder an another object.

In certain embodiments, the method includes measuring movement of the patient position and move the surgical tool holder based on said measured movement.

In certain embodiments, the one or more medical images comprise one or more of an MRI, CT, fluoroscopy, CT (ISO-C-3D) or 3D fluoroscopy medical image.

In certain embodiments, the one or more medical images comprise at least one of a pre-operative or an intra-operative medical image.

In certain embodiments, registering the patient is performed by the robotic surgical system automatically based at least in part on a patient navigation marker attached to the patient anatomy, and the one or more medical images.

In certain embodiments, registering the patient is performed using at least one or manual point-to-point registration, surface matching, and fluoroscopy-based registration.

In certain embodiments, the method includes providing, for display on a graphical user interface, the one or more projected trajectories comprises providing a list of trajectories, for display on a graphical user interface, the one or more projected trajectories.

In certain embodiments, providing, for display on a graphical user interface, the one or more projected trajectories comprises providing a preview of at least one of the one or more trajectories with the at least one of the one or more patient medical images.

In certain embodiments, the method includes moving a mobile cart transporting the robotic surgical system in proximity to an operating table; and stabilizing the mobile cart.

In certain embodiments, the method includes preventing, by the processor, movement of the end-effector unless a sensor on a handle of the robotic arm detects a hand of a user on the handle, thereby reducing the likelihood that the end-effector is moved unintentionally.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which.

Figure 1:
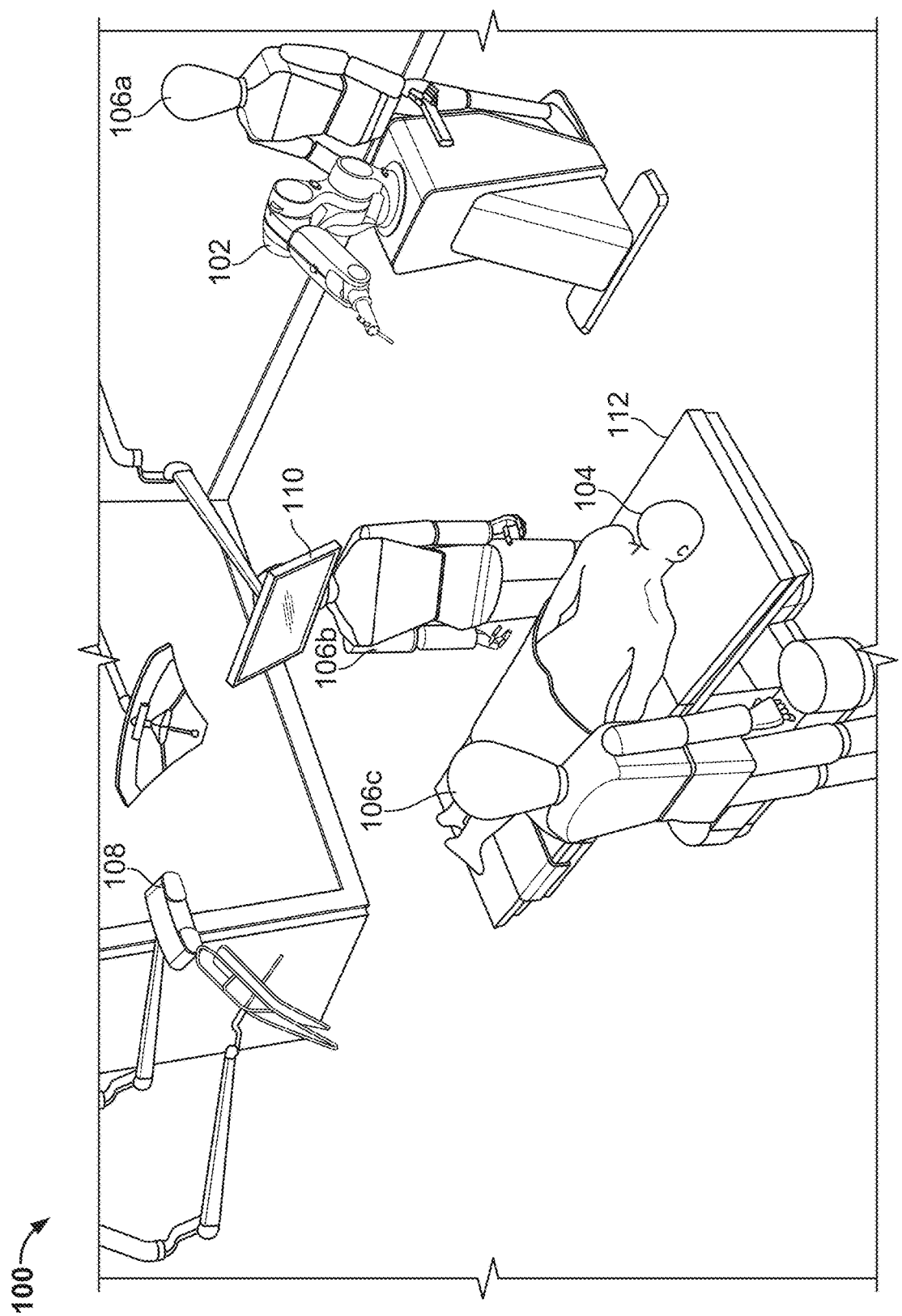
FIG. 1 is a diagram of an operating room in which a mobile cart housing a robotic system for a robotic-assisted spinal surgical procedure is positioned, in accordance with various embodiments of the disclosed technology.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE EMBODIMENTS

FIG. 1 illustrates an example surgical robotic system in an operating room 100. In some implementations, one or more surgeons, surgical assistants, surgical technologists and/or other technicians, (106a-c) perform an operation on a patient 104 using a robotic-assisted surgical system. One or more dilators may be used with the robotic surgical system to perform a minimally invasive surgery. The dilators may be used to provide a working channel through which the operation is performed. Standard dilators may be used with a robotic surgical system to provide precise guidance of surgical tools. A dilator may be held by the robot and automatically repositioned when the surgeon adjusts a trajectory for performing the surgery. The dilator itself may be used as a surgical instrument guide along with dilator adaptors that adjust the diameter of a portion of the dilator to allow for different sized tools to be guided by the dilator. Surgical instrument guides may also be held by the robotic arm such that tools are guided by a surgical instrument guide through the dilator to perform a medical procedure.

For example, first dilator may be used to access a vertebrae of a patient through the patient's muscles and skin. Subsequent dilators are configured to be positioned over the preceding dilators and increase the size of the working channel. Each dilator except the last added dilator is configured to be removed from the patient thereby leaving the last added dilator. The last added dilator is configured to be attached to an end effector of a robotic arm using a dilator fixator. In another example, the dilator inserted into the patient may be designed to expand thereby increasing the diameter of the working channel without adding additional dilators.

A manipulator is configured to allow robotically-assisted or unassisted positioning and/or movement of the last added dilator by a user with at least four degrees of freedom to align an axis defined by the last added dilator with respect to the vertebrae. Adjustment of the manipulator automatically adjusts an angle and/or position of the attached dilator with respect to the vertebrae and aligns an axis defined by the attached dilator with a desired trajectory during a surgical procedure without removal of the attached dilator from the patient tissue during the repositioning.

In some implementations, the surgical robotic system includes a surgical robot 102 on a mobile cart. The surgical robot 102 may be positioned in proximity to an operating table 112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

In some implementations, the footprint of the mobile cart is small (for example, no greater than 682 millimeters by 770 millimeters), thereby permitting improved access by a surgeon of both sides of an operating table at which the mobile cart is positioned during an operation.

The mobile cart may permit a user (operator) 106a, such as a technician, nurse, surgeon, or any other medical personnel in the operating room, to move the surgical robot 102 to different locations before, during, and/or after a surgical procedure. The mobile cart enables the surgical robot 102 to be easily transported into and out of the operating room 100. For example, a user 106a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

In some implementations, the wheels include a locking mechanism that prevents the cart from moving. The stabilizing, braking, and/or locking mechanism may be activated when the machine is turned on. In some implementations, the mobile cart includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector. Registration spatially aligns the robot, patient (e.g., spine) and the desired trajectory. A marker may be coupled or associated with a vertebrae or other bone to assist with the registration process. The location of the marker is determined by the system. The system stores this position. The position of the vertebrae is thus known. The position of other bones may also be determined with reference to the marker. Once the registration is complete, tracking and/or immobilization ensure that the registration (e.g., spatial orientation) is maintained Immobilization typically fixes the patient or bone (e.g., spine) with respect to the robot. In contrast, tracking system tracks the position of the patient or the bone (e.g., by tracking the movement of the marker or position of the marker relative to the robot) as described in relation to FIGS. 1 and 3.

In some implementations, the surgical robot 102 includes a robotic arm comprising joints allowing the arm to be automatically positioned upon user command into various different predetermined configurations convenient for various preparatory, readying, and storage procedures. For example, the surgical robot 102 may be arranged in a standby configuration. In a standby configuration, the robotic arm of surgical robot 102 may be arranged in a compacted standby configuration that, for example, facilitates easy and compact storage of surgical robot 102 when it is not in use. Other configurations may include a drape configuration in which the robot arm is extended to facilitate placement of a sterile surgical drape over the robot and cart, and a preparation configuration in which the robot arm is positioned prior to movement to the operating table whereupon more precise movement of the robot arm will be performed for alignment of the trajectory of the end effector (surgical tool holder).

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, when the surgical robot 102 is powered on, robot 102 switches from the standby configuration to another configuration, e.g., a preparation configuration. In some implementations, preset positions of the robotic arm and the arrangement of each moveable portion of the robotic arm of surgical robot 102 may be stored in a memory of the surgical system.

In some implementations, the mobile cart includes a power source for powering the robotic system, including, for example, the actuator. The power source may include a battery and/or a battery backup. In some implementations, the mobile cart is charged and/or powered by an electrical socket in the operating room. The mobile cart may be capable of being powered by a battery on the cart and/or via an electrical outlet. In some implementations, power is provided via an electrical outlet during the surgical procedure. A battery may be used to provide power to the system when the system is being moved or in case of a power cut.

In some implementations, different elements of the surgical system work in tandem by communicating with each other wirelessly. In some implementations, a tracking detector 108 monitors the location of patient 104 and the surgical robot 102. The tracking detector may be a camera, a video camera, an infrared detector, field generator and sensors for electro-magnetic tracking or any other motion detecting apparatus. In some implementation, based on the patient and robot position, the display screen displays a projected trajectory and/or a proposed trajectory for the robotic arm of robot 102 from its current location to a patient operation site. By continuously monitoring the patient and robotic arm positions, using tracking detector 108, the surgical system can calculate updated trajectories and visually display these trajectories on display screen 110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure.

For safety reasons, the mobile cart is provided with a stabilization system that may be used during a surgical procedure performed with a surgical robot. The stabilization mechanism increases the global stiffness of the mobile cart relative to the floor in order to ensure the accuracy of the surgical procedure. An example of the robotic surgical system discussed and used herein is described in U.S. patent application Ser. No. 14/266,769, filed Apr. 30, 2014, entitled "Apparatus, Systems, and Methods for Precise Guidance of Surgical Tools," which is hereby incorporated by reference in its entirety.

Figure 2A:
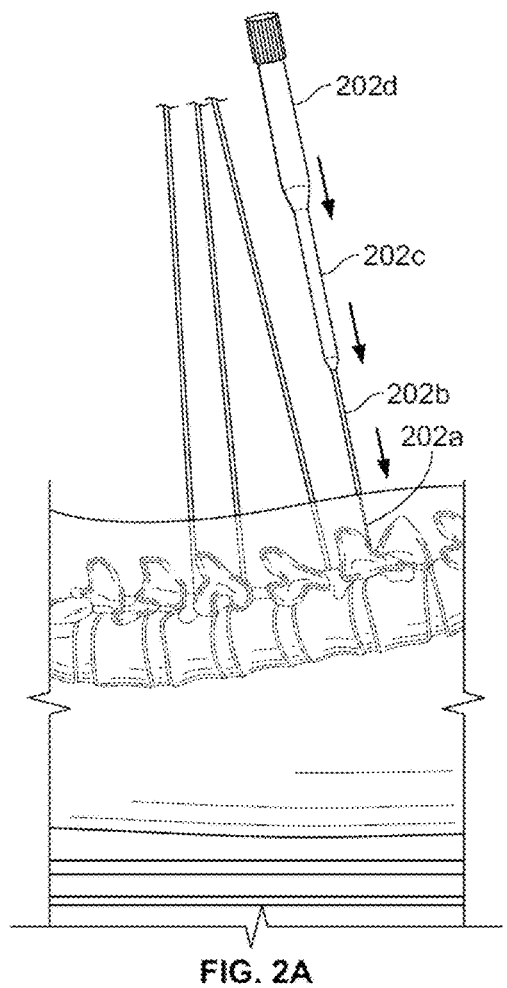
FIGS. 2A-B are illustrations of an example set of dilators used for performing a minimally invasive surgical procedure.
Figure 2B:
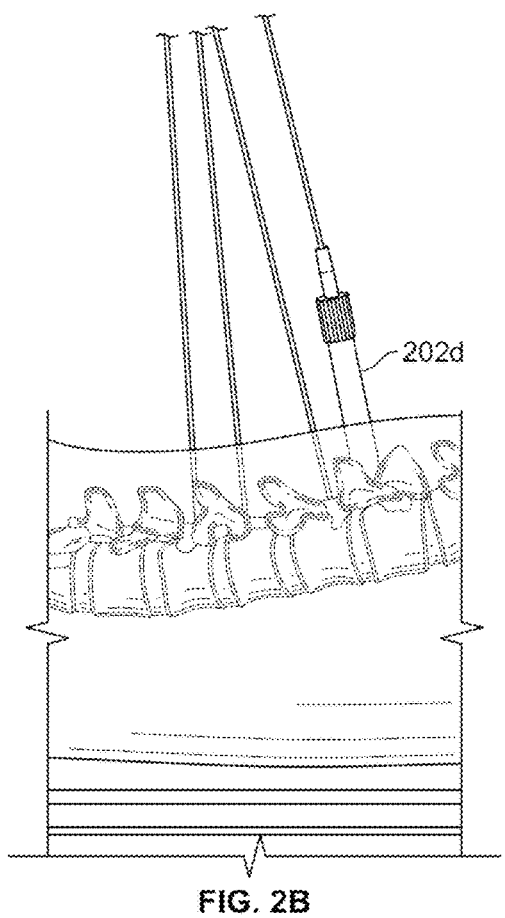

FIGS. 2A-B are illustrations of an example set of dilators 202 used for performing a minimally invasive surgical procedure. Dilators 202 may be used to achieve a working channel for surgical instruments. The dilators may be inserted manually by a surgeon one by one until the surgeon obtains the required diameter of the working channel. For example, a first dilator 202a may be inserted at the access point. The first dilator 202 may be a hollow tube-like device (similar to the other dilators 202b-d) or it may be a solid tube-like device for marking the access point. The second dilator 202b maybe added over the first dilator 202a. Similarly, the third dilator 202c may be added over the second dilator 202b to further increase the size of the working channel. Each dilator added after the first dilator 202a increases the size of the working channel. In this example, the fourth dilator 202d is added over the third dilator 202c. In some implementations, dilators may be removed after the next dilator is added. For example, the second dilator 202b may be removed after the third dilator 202c is added. In some implementations, dilators may be removed after the last dilator is added. For example, previously added dilators may be removed after the last dilator 202d is added, thereby leaving a working channel the diameter of the forth dilator 202d.

Figure 3:
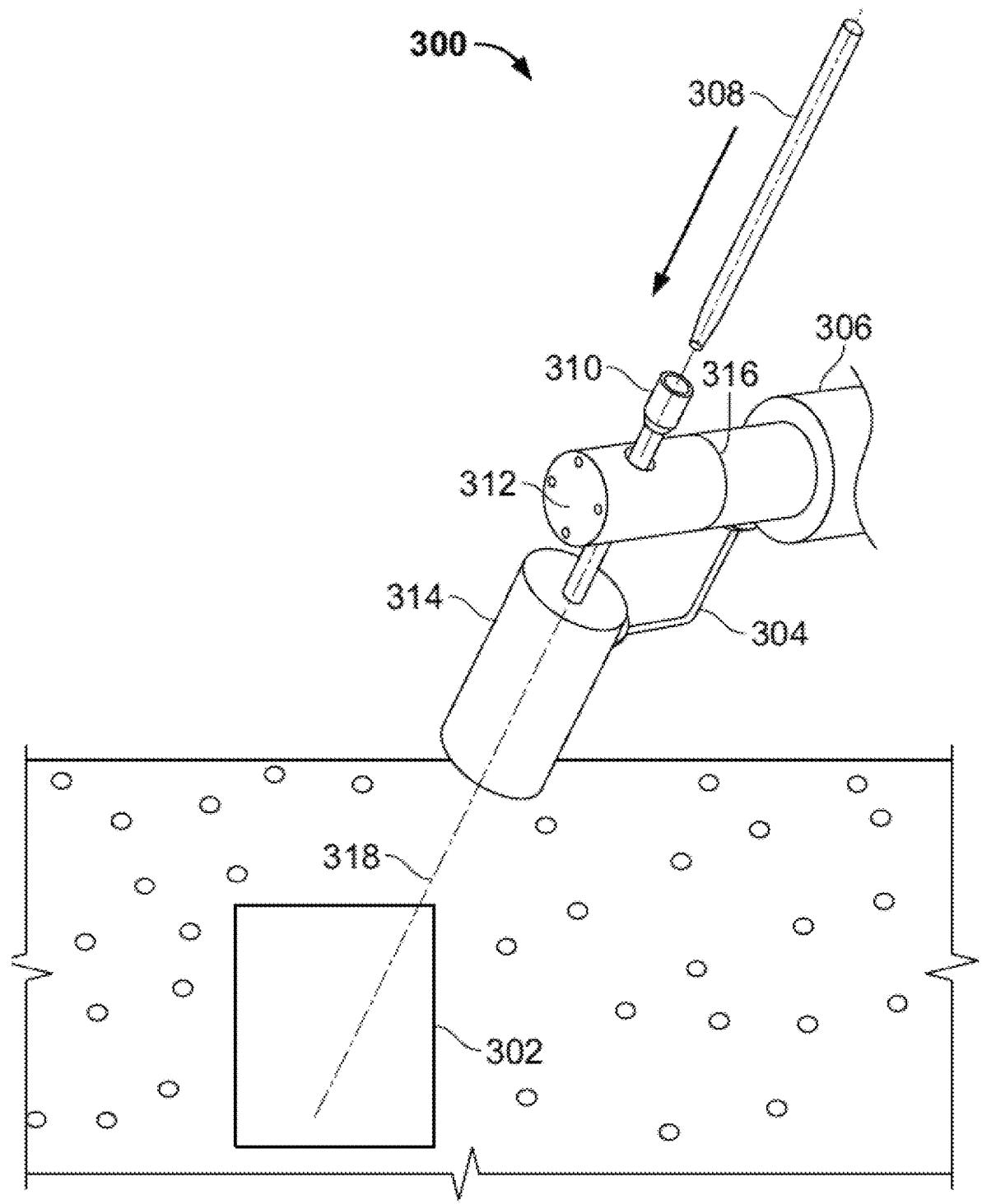
FIG. 3 is an illustration of an example robotic surgical system using a dilator.

The dilators may be used with a robotic surgical system, for example, as shown in FIG. 3. FIG. 3 is an illustration of an example robotic surgical system 300 using a dilator 314. The surgeon may manually obtain access to the vertebrae 302 through the skin and muscles. After applying the dilators as described in relation to FIGS. 2A-B, the internal dilators may be removed, leaving the largest one 314. The robot 306 may be moved closer to the patient and attached to the dilator 314 using the dilator fixation 304. In some implementations, a tool guide 310 held by a tool holder 312 fits inside the dilator 314. The tool guide 310 may be used to guide a surgical instrument 308 to access the vertebrae 302 via the working channel formed by the dilator 314. For example, the tool guide 310 may be used to prepare a hole in vertebrae of a patient. The tool holder 312 may be attached to the may be attached to the robot 306 via a tool holder attachment 316. In some implementations, the dilator 314 itself acts as a tool guide.

In some implementations, standard dilators may be used with the robotic surgical system to provide a precise solution to guide surgical tools. For example, in contrast to surgeries using passive arms to hold the dilator, the dilator may be held by the robotic surgical system and the dilator may be automatically repositioned in response to the surgeon changing the trajectory 318.

A manipulator of the robotic surgical system is configured to allow robotically-assisted or unassisted positioning and/or movement of the dilator attached to the end effector (e.g., the last added dilator) by a user with at least four degrees of freedom to align an axis defined by the dilator attached to the end effector with respect to the vertebrae. The robotic arm is configured to be maneuvered to a desired position to align an axis defined by the surgical instrument guide at a desired trajectory in relation to the vertebrae. The dilator connected to the end effector of the robotic arm is automatically positioned as the robotic arm is maneuvered to adjust to the desired trajectory. Adjustment of the manipulator automatically adjusts an angle and/or position of the attached dilator with respect to the vertebrae and aligns an axis defined by the attached dilator with a desired trajectory during a surgical procedure without removal of the attached dilator from the patient tissue during the repositioning.

Figure 4:
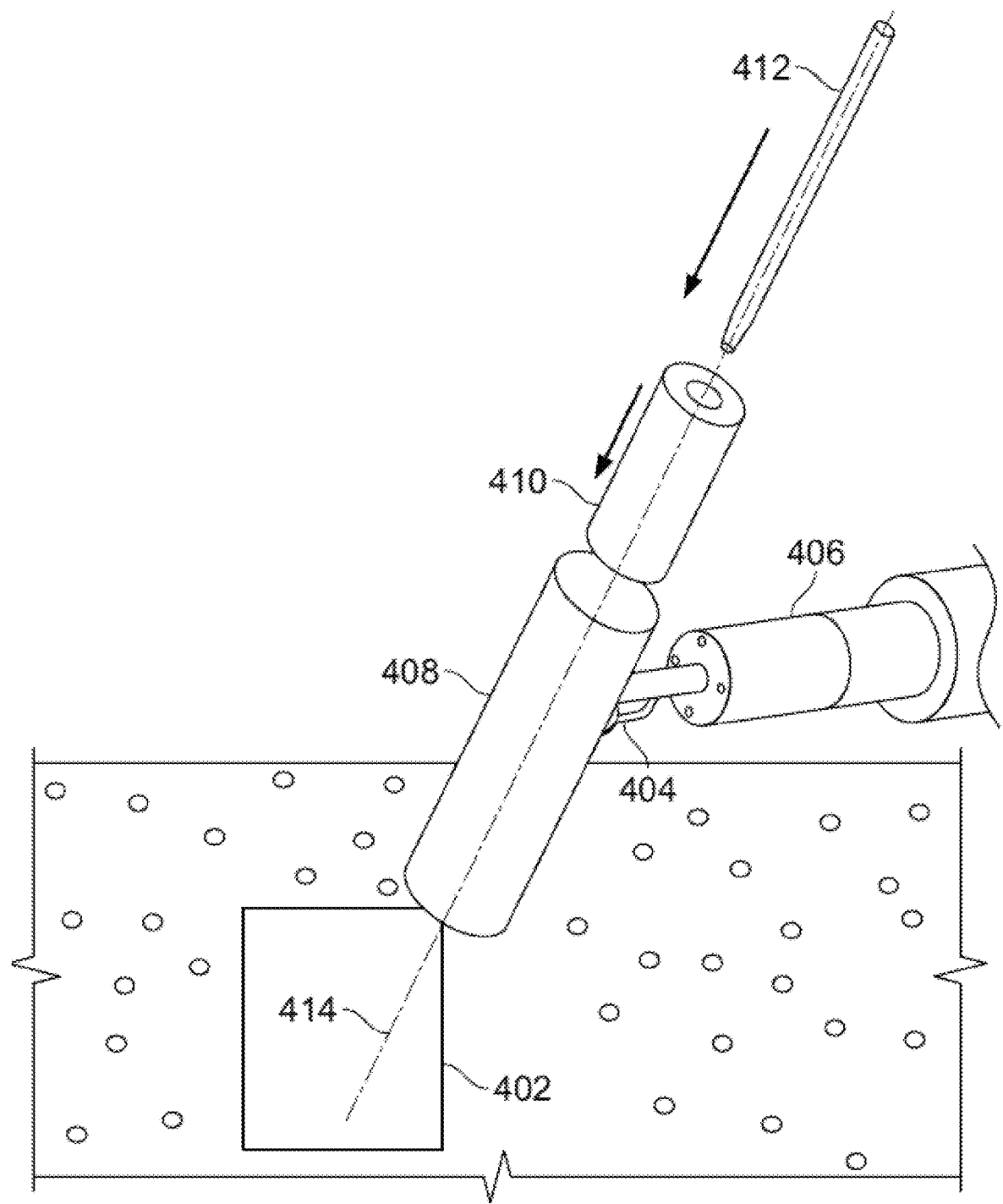
FIG. 4 is an illustration of an example robotic surgical system for performing minimally invasive surgery using a guided dilator.

FIG. 4 is an illustration of an example robotic surgical system for performing a minimally invasive surgery using a guided dilator. The surgeon may manually obtain access to the vertebrae 402 through the skin and muscles. After applying the dilators as described in relation to FIGS. 2A-B, the internal dilators may be removed, leaving the largest one 408. The robot 406 may be moved closer to the patient and attached to the dilator 408 using the dilator fixation 404. The dilator 408 is designed to guide a surgical tool 412. A dilator adapter 410 may be used to allow different size tools to be used with the dilator 408.

In some implementations, standard dilators may be used with the robotic surgical system to provide a precise solution to guide surgical tools. For example, in contrast to surgeries using passive arms to hold the dilator, the dilator may be held by the robotic surgical system and the dilator may be automatically repositioned in response to the surgeon changing the trajectory 414.

Figure 5:
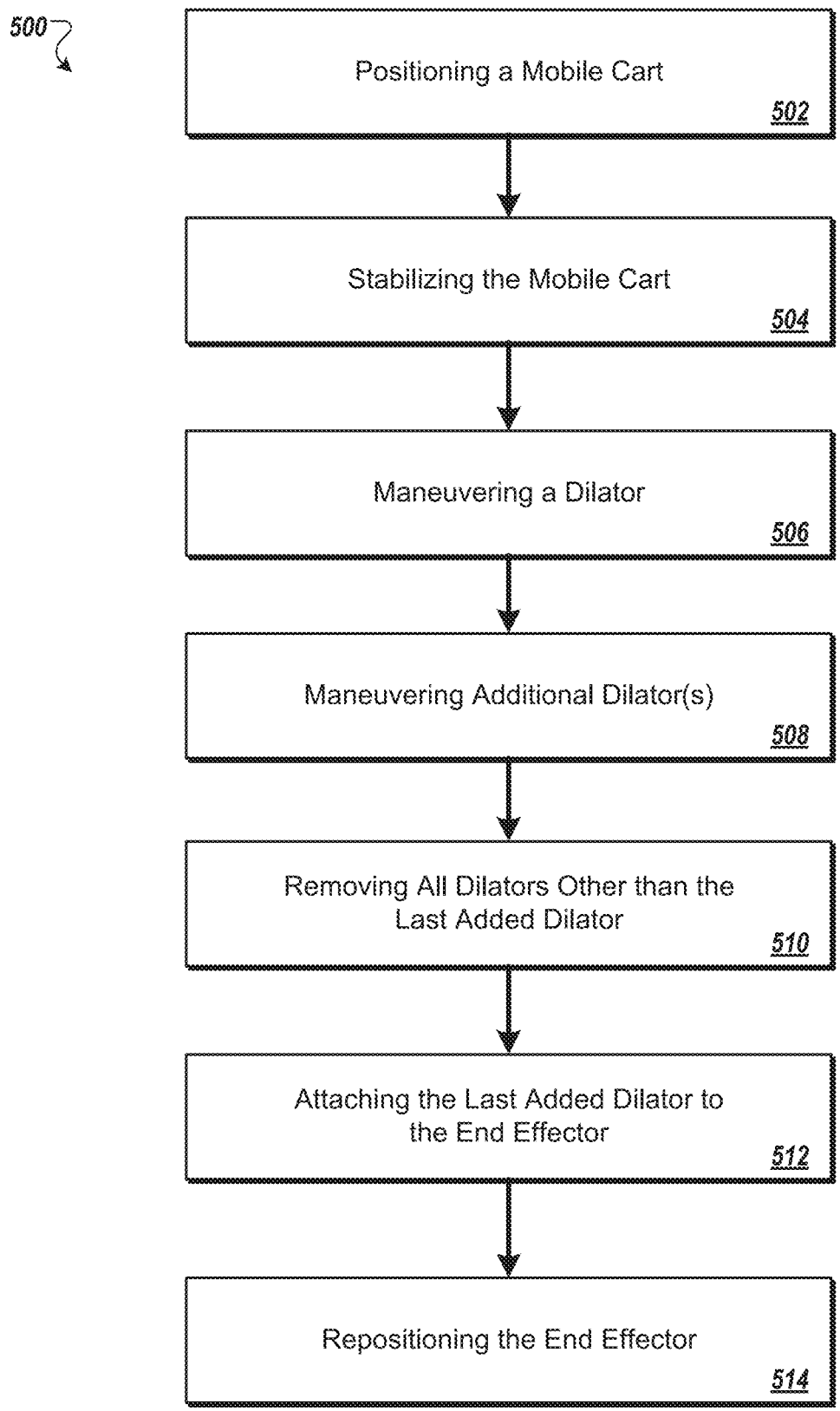
FIG. 5 is a flowchart of an example method of performing minimally invasive spinal surgery with a robotic surgical system.

FIG. 5 is a flowchart of an example method 500 of performing minimally invasive spinal surgery with a robotic surgical system. In some implementations, the method may include positioning a mobile cart (502) transporting a robotic surgical system. The robotic surgical system may include a robotic arm in proximity to an operating table. The robotic arm may have an end effector. After positioning the mobile cart, the mobile cart may be stabilized (504).

The method 500 may include maneuvering a dilator to access a vertebrae of a patient through the patient's muscles and skin (506). The dilator may define a working channel for accessing the vertebrae. Additional dilators may be placed over earlier placed dilator(s) (508) to increase the size of the working channel. All dilators except the last added dilator may be removed (510) thereby leaving a working channel of a desired diameter for the surgery.

For example, a second dilator may be maneuvered to slide over the dilator. The second dilator may be sized and shaped to slide over the dilator and increase the size of the working channel. After positioning the second dilator over the dilator (and/or after positioning one or more subsequent dilators over the preceding dilators), the dilator (and/or other dilators except the final added dilator) may be removed from the patient, thereby leaving the last added dilator.

The method 500 may include attaching a dilator to the end effector of the robotic arm using a dilator fixator (512). In some implementations, the dilator attached (or to be attached) to the end effector is the dilator with largest circumference. Following attachment of the dilator to the end effector, the end effector may be repositioned to adjust the angle and/or position of the attached dilator with respect to the vertebrae (514). The robotic arm may be maneuvered to a desired position to align an axis defined by the surgical instrument guide at a desired trajectory in relation to the vertebrae. This causes the dilator connected to the end effector of the robotic arm to be automatically positioned as the robotic arm is maneuvered to adjust to the desired trajectory.

In some implementations, a surgical instrument guide is placed inside of the dilator attached (or to be attached) to the end effector. The surgical instrument guide (e.g., drill bit guide, tap guide, screwdriver guide, screw guide, awl guide, and implant guide) is sized and shaped to fit at least partially inside the dilator along an axis defined by the dilator and is configured to hold and/or restrict movement of a surgical instrument (e.g., drill bit, pedicle finder, screw-based implant, awl, surface-pointing device, screw based implant, screw driver, tap, implants, implants with extenders, or other similar instruments) therethrough. The surgical instrument may be, for example, a tap such as the StealthStation® CR Horizon Legacy Taps from Medtronic, Inc. of Minneapolis, Minn. or a universal surgical tools system (e.g., Medtronic's NavLock system). In some implementations, the dilator itself is used as a surgical instrument guide. The dilator may be configured to hold and/or restrict movement of a surgical instrument therethrough. Dilator adapters may be used to allow different size instruments to be guided by the dilator.

Figure 6:
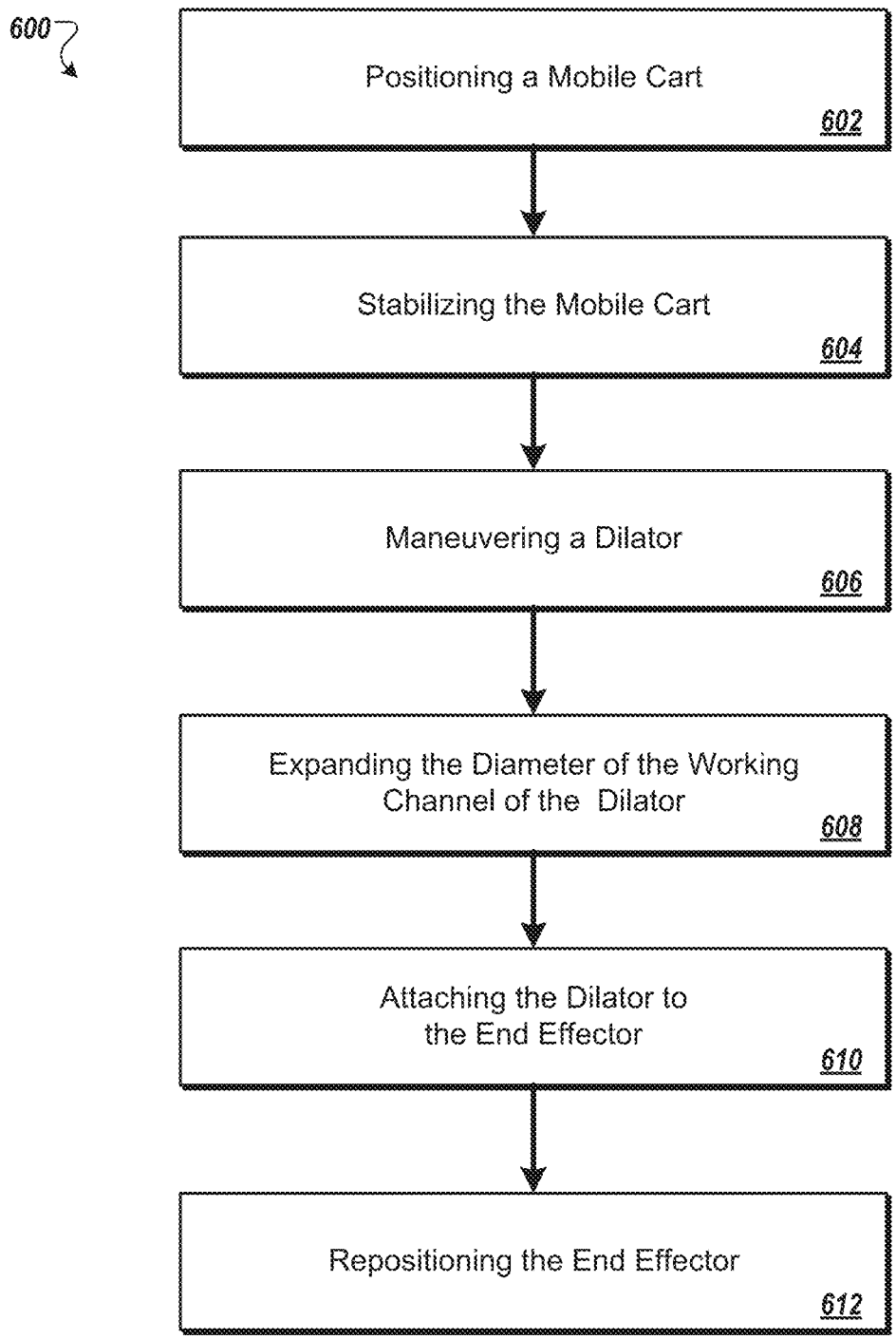
FIG. 6 is a flowchart of an example method for performing minimally invasive surgery using minimally invasive surgical techniques.

FIG. 6 is a flowchart of an example method 600 for performing minimally invasive surgery. In some implementations, the method may include positioning a mobile cart (602) transporting a robotic surgical system. The robotic surgical system may include a robotic arm in proximity to an operating table. The robotic arm may have an end effector. After positioning the mobile cart, the mobile cart may be stabilized (604).

The method 600 may include maneuvering a dilator to access a vertebrae of a patient through the patient's muscles and skin (606). The dilator may define a working channel for accessing the vertebrae. The diameter of the working channel of the dilator may be expanded (608). For example, the dilator may be configured such that the diameter of the dilator may be increased. Thus, the size of the working channel may be increased without the use of multiple dilators.

The method 600 may include attaching the dilator to the end effector of the robotic arm using a dilator fixator (610). Following attachment of the dilator to the end effector, the end effector may be repositioned to adjust the angle and/or position of the attached dilator with respect to the vertebrae (612).

Figure 7:
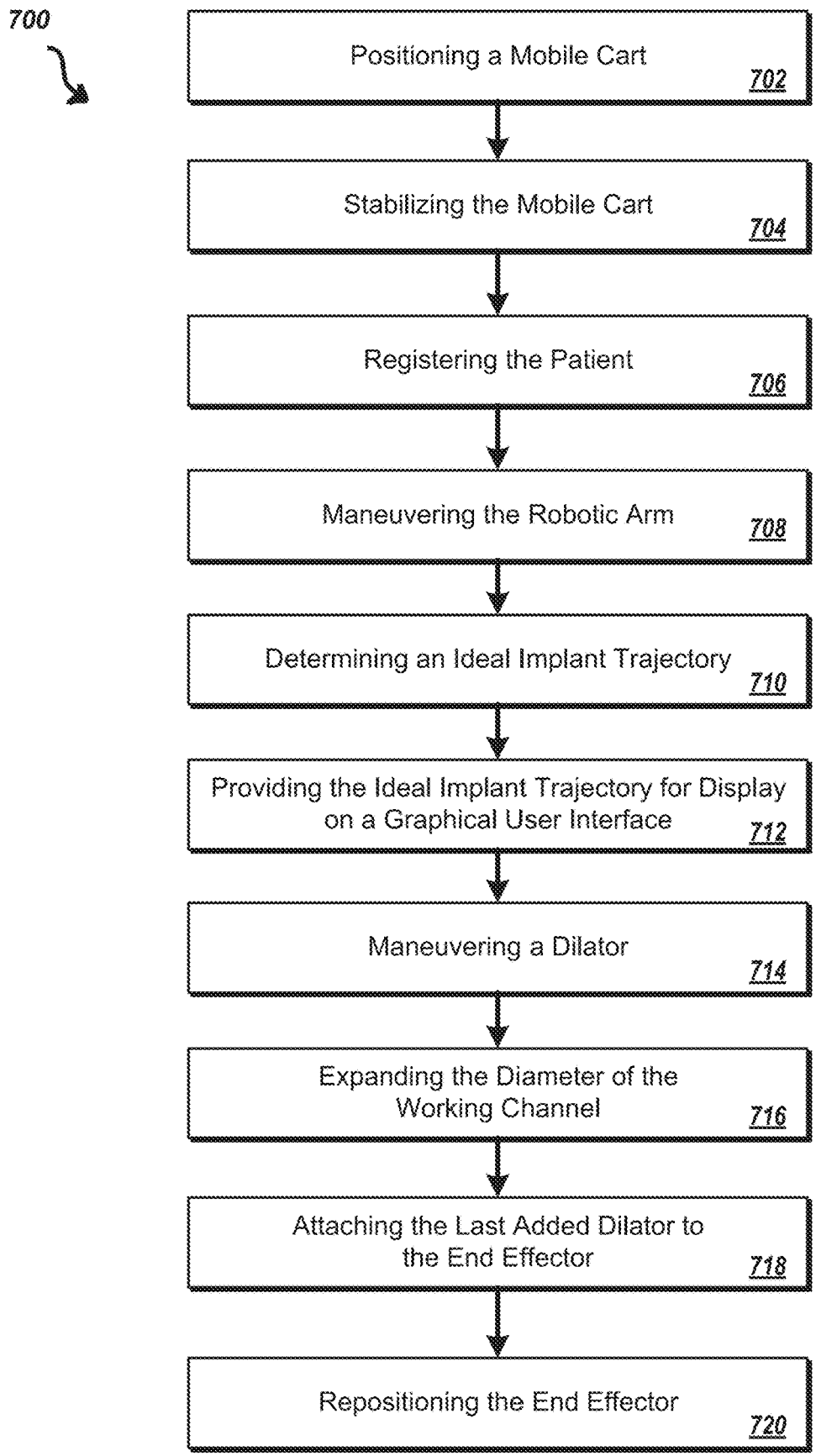
FIG. 7 is a flowchart of an example method for performing minimally invasive surgery using minimally invasive surgical techniques.

FIG. 7 is a flowchart of an example method 700 for performing minimally invasive surgery using minimally invasive surgical techniques. In some implementations, the method may include positioning a mobile cart (702) transporting a robotic surgical system. The robotic surgical system may include a robotic arm in proximity to an operating table. The robotic arm may have an end effector. After positioning the mobile cart, the mobile cart may be stabilized (704).

The method 700 may include registering the patient (706). Registering the patient may include identifying the transformation between the actual patient anatomy and one or more medical images. Registering the patient may include identifying a correlation between the surgical anatomy of the patient in the "real world" and a medical image (e.g., an image acquisition during surgery). Registration may also be accomplished using co-registration (e.g., former studies). The robotic arm may be maneuvered towards the vertebrae on which the surgeon will operate (708). In some implementations, the robotic surgical system will recognize the vertebra on which the surgeon wishes to operate as the robotic arm is maneuvered towards the vertebra. A processor of a computing device may determine an ideal implant trajectory (710). The system allows for a desired trajectory (e.g., for a drill guide during spinal surgery) to be set in a variety of manners based on the circumstances of the surgery. For example, some surgical procedures are planned pre-operatively with the surgeon defining the desired position of an implant using imaging technology, such as CT images (e.g., 3D CT images). The desired position of the implant may also be determined and proposed by the system. In the operating room the surgeon may be guided by the robotic system (e.g., robotic guidance of the surgical tools) to accurately execute the planning.

The ideal implant trajectory may be displayed on a graphical user interface for review by the surgeon (712). The surgeon may adapt the ideal implant trajectory if needed using hands-on planning. The surgeon acknowledges the ideal implant trajectory or the adapted trajectory thereby causing the acknowledged trajectory to be stored as the desired trajectory.

The method 700 may include maneuvering a dilator to access a vertebrae of a patient through the patient's muscles and skin (714). The dilator may define a working channel for accessing the vertebrae. The diameter of the working channel may be expanded (716) using the techniques as described in relation to FIGS. 5 and 6. The method 700 may include attaching the dilator to the end effector of the robotic arm using a dilator fixator (718). Following attachment of the dilator to the end effector, the end effector may be repositioned to adjust the angle and/or position of the attached dilator with respect to the vertebrae (720).

Having described various embodiments of the disclose technology, it will now become apparent to one of skill in the art that other embodiments incorporating the concepts may be used. It is felt, therefore, that these embodiments should not be limited to the disclosed embodiments, but rather should be limited only by the spirit and scope of the following claims.

Figure 8:
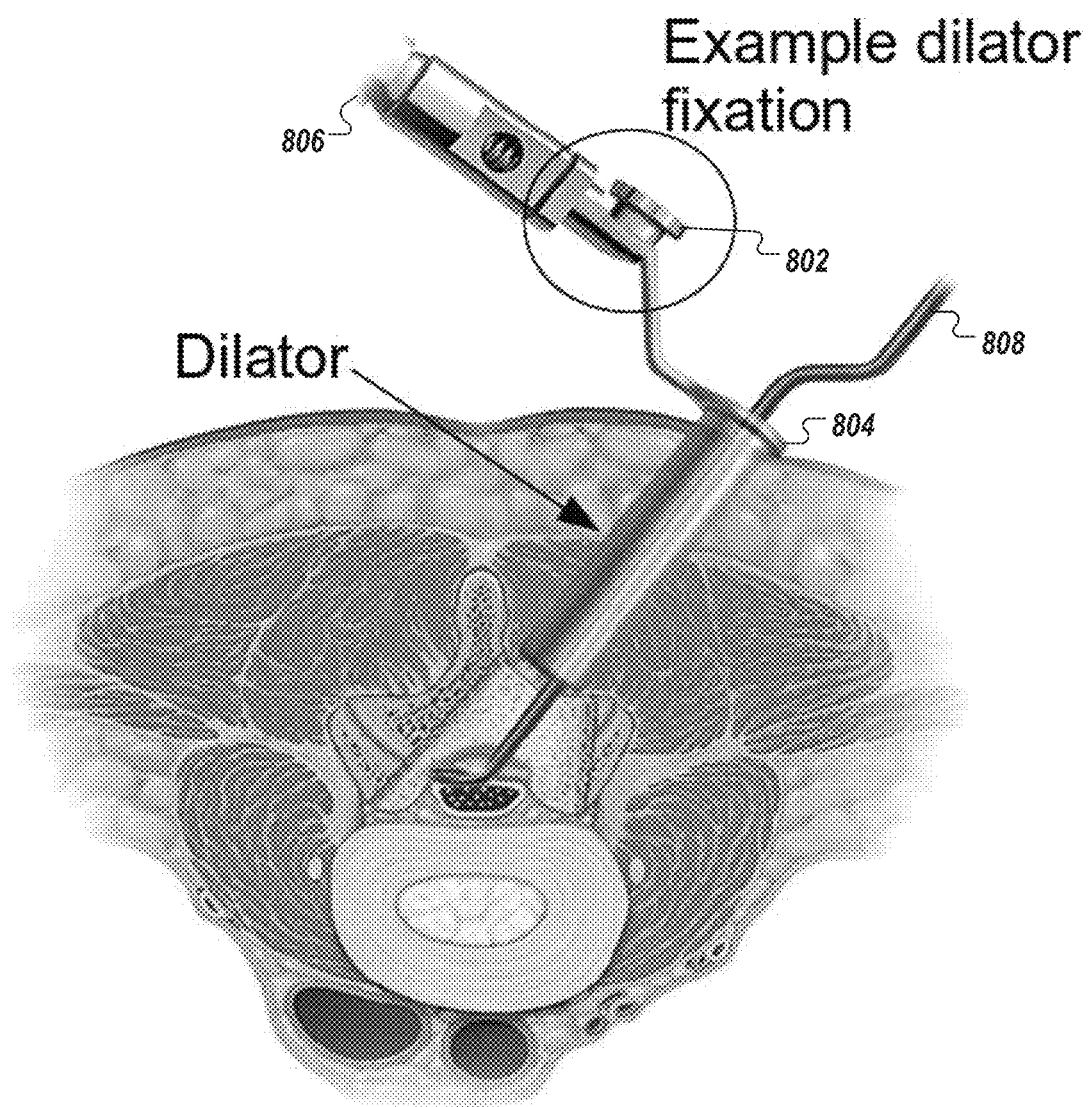
FIG. 8 is an illustration of an example dilator fixation for attaching a dilator to a robotic arm.

FIG. 8 is an illustration of an example dilator fixation 802 for attaching a dilator 804 to a robotic arm 806. The dilator fixation 802 may be mechanically coupled to the robotic arm 806 such that the dilator fixation is rigidly coupled to the robotic arm 806. For example, the dilator fixation 802 maybe bolted to the robotic arm 806 such that the dilator fixation 802 will not move relative to the robotic arm 806 thereby allowing the robot to always knows the position of the dilator fixation 802. The dilator fixation 802 may provide a quick-release mechanism to rigidly secure the dilator 804 to the robotic arm 806. In some implementations, the dilator 804 and dilator fixation 802 are formed as one piece and attached to the robotic arm 806 via a bolt, screw, or quick-release mechanism. The attachment system may be designed such that the dilator 804 may be removed quickly and easily (e.g., toollessly).

Figure 9:
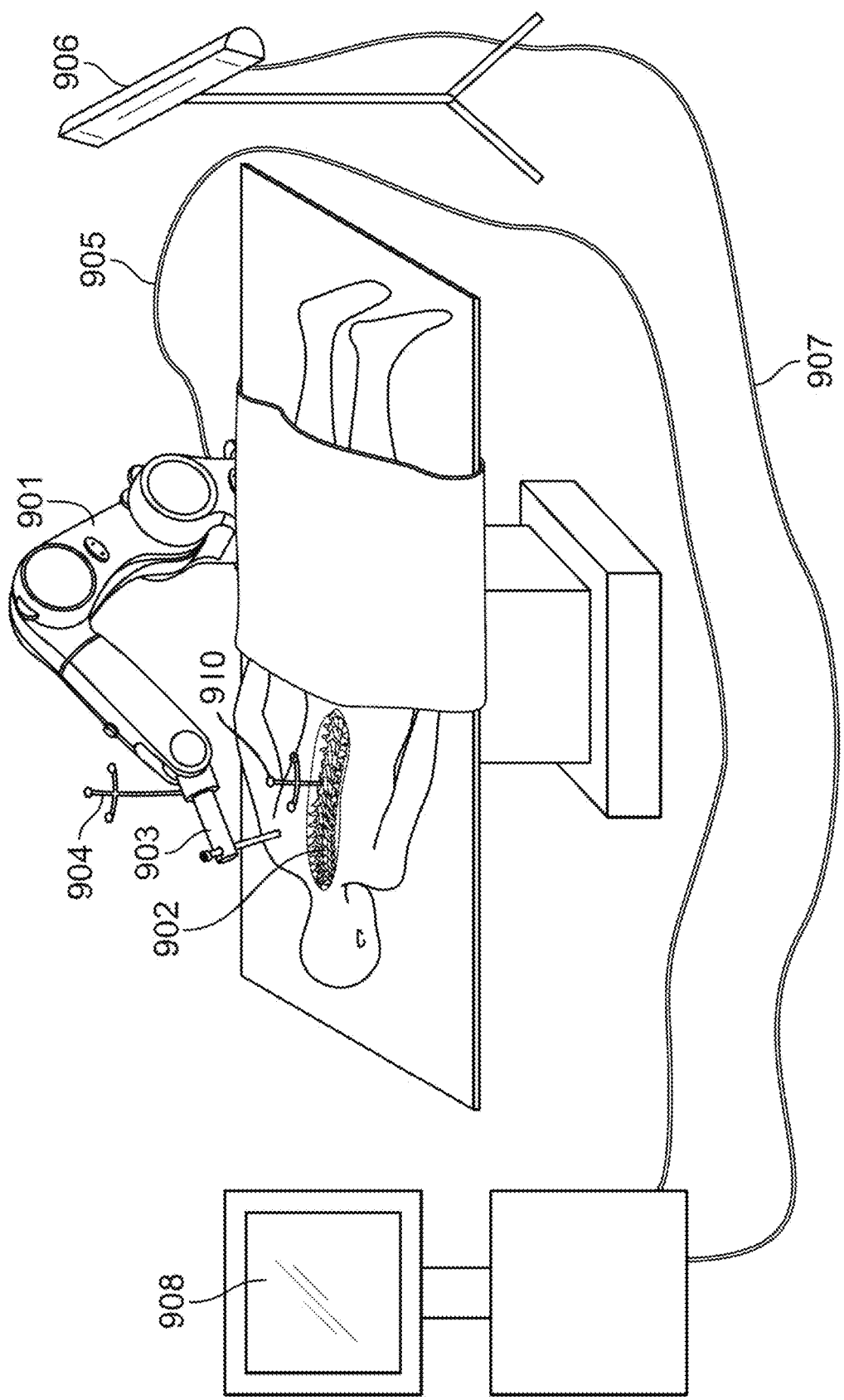
FIG. 9 is an illustration of a system for robotic integration with automatic planning.
Figure 10:
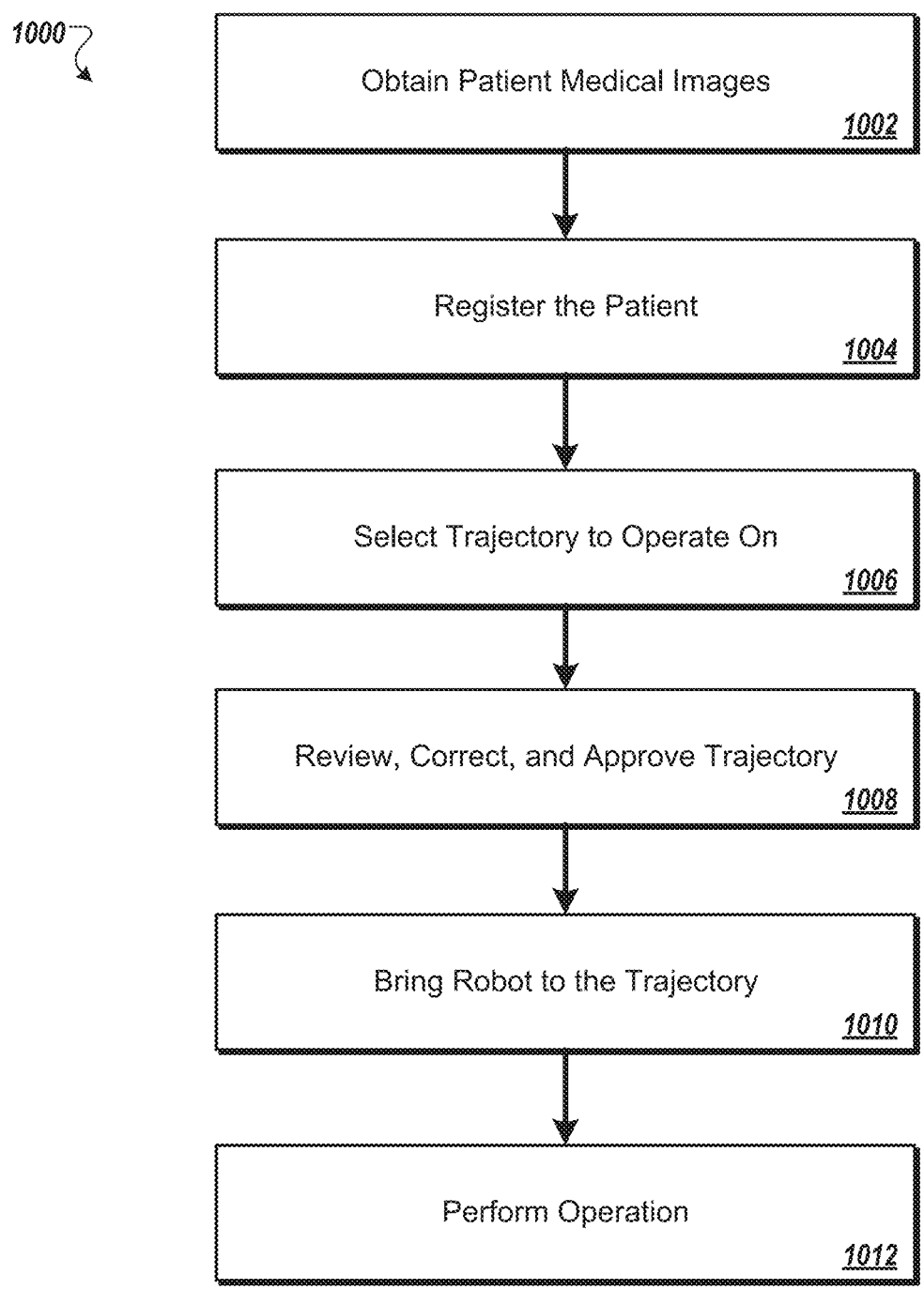
FIG. 10 illustrates a flow chart of a method 1000 of performing minimally invasive surgery using automatic planning.

FIG. 9 is an illustration of a system for robotic integration with automatic planning, for example, as described in relation to FIG. 10. The system, in certain embodiments, includes a robot arm 901, a patient vertebrae 902 (e.g., with a patient navigation marker 910 attached), a robot tool holder with tool guide 903, a robot navigation marker 904, a tracking camera 906, a connection to the tracking camera 907, a navigation system 908, and a connection to robot-navigation 905. In certain embodiments, a navigations marker, such as patient navigation marker or robot navigation marker 904, is a rigid body with reflective spheres which is attached to an item, such as a robot end effector or patient vertebrae. A navigation system or tracker measures positions of each sphere using stereoscopic cameras and triangulation. By assembling the positions of spheres together with marker geometry, the translation and rotation of the marker in space is known. After the process of registration the system knows the location of the marked item, such as the end-effector or patient vertebrae in reference to the marker thus by tracking the marker or patient frame we know where the marked item is located.

FIG. 10 illustrates a flow chart of a method 1000 of performing minimally invasive surgery using automatic planning. In certain embodiments, automatic planning includes obtaining patient medical images (1002). In this step (1002) medical images of the patient are obtained. These medical images can come from MRI, CT, fluoroscopy, CT (ISO-C-3D, such as Siemens ISO-C 3D C-Arm) or 3D fluoroscopy (e.g., 0-Arm Surgical Imaging System by Medtronic, Inc. of Minneapolis, Minn., the Artis Zeego by Siemens Medical Solutions USA, Inc. of Malvern, Pa.). The images can be obtained pre-operatively, as it is often the case for MRI or CT, or intra-operatively which is the case for fluoroscopy and 3D fluoroscopy.

Next, the patient is registered (1004). Registration is accomplished by finding the transformation between actual patient anatomy and medical images. This can be done automatically for intra-operative medical imaging. In this case the patient navigation marker 910 is attached to the vertebrae 902 before images are taken. A similar patient navigation marker 910 is attached to the medical imaging device. The patient navigation marker 910 is recognized by the software on the images and by knowing the position of imaging device, medical images can be related to the position of the patient navigation marker 910 for further usage.

There are several alternative approaches for registering the patient and these include manual point-to-point registration, surface matching, and fluoroscopy-based registration (e.g., intraoperative fluoroscopic images are matched to pre-operative CT images).

Next, a trajectory to operate on is selected (1006). Planning of the trajectory can come from different sources. It can be prepared pre-operatively by the surgeon, his assistant, external company, or other parties.

For certain systems the trajectory can be planned automatically based on medical images. An automatic planning algorithm takes these medical images as an input and based on these medical images it recognizes the vertebrae and proposes the most suitable trajectories (e.g. a single trajectory or multiple trajectories, each of which may be a viable option).

In this step (1006) the surgeon identifies for the system which vertebra(e) he/she would like to operate on. This can be accomplished in a variety of manners, including the presentation of the list of trajectories (e.g., on a display) for selection by the surgeon. In certain embodiments, the user is able to preview trajectories on medical images and based on these decide which trajectory to use.

An alternative way of selecting the trajectory is based on user pointing the actual patient vertebrae and the system automatically presenting the trajectory/trajectories located the closest to this place. This provides a very intuitive and user friendly approach. The user can use various means for indicating the vertebrae/surgical spot he/she would like to operate on. For example, the user can use robotic arm whose position is known to the system. The user can use any navigated surgical instrument as well, including a navigation pointer, navigated screwdriver, navigated drill, as well as other device. In this embodiment, the system automatically "discovers" or "guesses" the intention of the surgeon and presents him the best option for the trajectory to the surgeon.

Next, the surgeon reviews, corrects (if applicable) and approves the trajectory (1008). The surgeon, in certain embodiments, has the ability to review the trajectory. This can be accomplished by providing the surgeon with medical images with a virtual projection of the trajectory thereon (e.g., on a display of the robotic surgical system). Typically a surgeon uses three medical views to review the trajectory (e.g. sagittal, axial and coronal view), but other views can be used as well (e.g., other views and more or less views).

In certain embodiments, the system provides a follow view that shows an image (e.g., animated image) following the trajectory in the view perpendicular to the trajectory axis to make sure that there is enough bony structures on each side for the trajectory to hold the implant.

In certain embodiments, the surgeon corrects the trajectory based on the review. The trajectory can be corrected using hands-on planning mode. A discussion of hands on planning can be found in U.S. patent application Ser. No. 14/266,769, filed Apr. 30, 2014, entitled "Apparatus, Systems, and Methods for Precise Guidance of Surgical Tools," which is hereby incorporated by reference in its entirety. Alternatively, the trajectory can be corrected using navigated instruments to point to a better trajectory, thereby correcting/replacing the previous trajectory. Alternatively, the trajectory can be corrected by redoing automatic planning with different input parameters or manually defining trajectory on the computer screen.

In certain embodiments, the surgeon is given the ability (direct, e.g. via acknowledgement button, or indirect, if surgeon proceeds, it means that he is OK) to approve the trajectory. In certain embodiments, the method proceeds without the surgeon approving the trajectory.

Next, the robot arm 901 is brought to the trajectory (1010). Usually it is difficult for the surgeon to find the real trajectory in space when shown only with the indications on the computer screen. In certain embodiments, the disclosed technology assist the surgeon in finding the trajectory using the robot 901. This represents a great usability improvement as it simplifying a user task, improves safety as the robot can be more reliable than a human in spatial location, and improves efficiency because robot can quicker find the trajectory than the user and thus save time in the operating room.

In certain embodiments, the robot can automatically move the trajectory following user request (e.g., and in certain embodiments, with user supervision). However, automatic movement by the robot is dangerous in an operating room as typically the robot only has partial knowledge of the surrounding environment which makes collisions possible (and probable as the operating room is highly unstructured environment). As such, the disclosed robot, in certain embodiments, is equipped in force sensor. The force sensor can be used to discover/identify collisions by an increase of forces (e.g., if the force sensor is expecting to measure no force, the system can detect a collision if a force is detected). Similarly, additional sensors (e.g., artificial skin, laser scanner, electrical/capacitive proximity sensors, etc.) can be added on the robotic arm with a goal of detecting a collision. Upon detecting a collision, the robot shall react accordingly, such as stopping or adapting the trajectory of movement (e.g. move the robot arm segments up if these are the lower sensors detecting collision).

In some embodiments, rather than using automatic movement, the surgeon is required to move the robot "manually", as in hands-on planning. However, the robot may still provide the surgeon with assistance in finding the trajectory by providing haptic feedback (e.g., force and/or torque). This assistance can be provided by simulating attractive forces/torques to guide the surgeon to bring the robot to the target position. In certain embodiments, these forces/torques make it easier to move to the direction of correct trajectory while preventing/making difficult to move in the other direction (e.g., the latter, by providing resistive forces). For example, spring-like forces (proportional to the distance) or magnetic-like forces (proportional to square of the distance) may be used to guide the user to the trajectory. The haptic feedback may be delivered to the user (e.g., surgeon) by an actuator associated with the robotic arm, controlled by a processor. The amount (intensity) of force feedback to be delivered to the user may be computed in real-time as a function of the position of the robotic arm in relation to the computed correct trajectory. The haptic feedback may be computed and delivered in relation to a haptic guide, where the haptic guide provides constraints to particular regions, points, and/or surfaces, or the haptic guide may provide detents or force fields to encourage movement toward a particular position in 3D space at a particular orientation (yaw, pitch, roll).

Once the robot is along the correct trajectory, it can be locked to it. In certain embodiments, the user is allowed to move the end effector only along the trajectory (e.g., if it is a line in space) or rotate along trajectory if the rotation of the tool is not important. In certain embodiments, when user tries to move out of the trajectory, he/she feels repulsive forces preventing him/her from doing so.

The surgeons shall know when he/she is precisely (or with certain pre-defined error margin) along the trajectory. It can be implemented using visual feedback, such as a green light interface when precision can be assured and/or an alarm when the surgeon moves out of the trajectory (e.g., audible alarm).

In certain embodiments, once positioned along the trajectory, the robot might come out of align with the trajectory, for example, due to movement of the patient (e.g., breathing), forces applied to the vertebrae, or movement of the whole table. In this case, the appropriate mode may be activated to provide assistance in finding the trajectory again to lock the robot into the correct, new trajectory. In certain embodiments, the movement (e.g., of the patient or table) is measured and the robot reacts to the movement automatically (e.g., the system tracks the vertebra(e)). For example, the robot, in certain embodiments, provides real-time compensation to follow the movement of the vertebra(e). A discussion of tracking of the vertebrae is provided in U.S. patent application Ser. No. 14/522,509, filed Oct. 23, 2014, entitled "Robotic System and Method for Spinal and Other Surgeries," which is hereby incorporated by reference in its entirety, and U.S. patent application Ser. No. 14/266,769, filed Apr. 30, 2014, entitled "Apparatus, Systems, and Methods for Precise Guidance of Surgical Tools."

Next, the operation is performed (1012). This may include drilling a hole and inserting an implant in the hole, as well as other steps. A discussion of performing the operation using a surgical robot is described in U.S. patent application Ser. No. 14/266,769, filed Apr. 30, 2014, entitled "Apparatus, Systems, and Methods for Precise Guidance of Surgical Tools."

As explained below, steps for any method discussed herein can be done in a different order. For example, the robotic arm 901 can be brought to the trajectory (e.g., step 1010 in FIG. 10) before reviewing, correcting, and approving the trajectory (e.g., step 1008 in FIG. 10). For example, if a surgeon wants to use the robot to correct the trajectory plan, the robotic arm 901 may be brought to the trajectory before correcting the trajectory.

Figure 11:
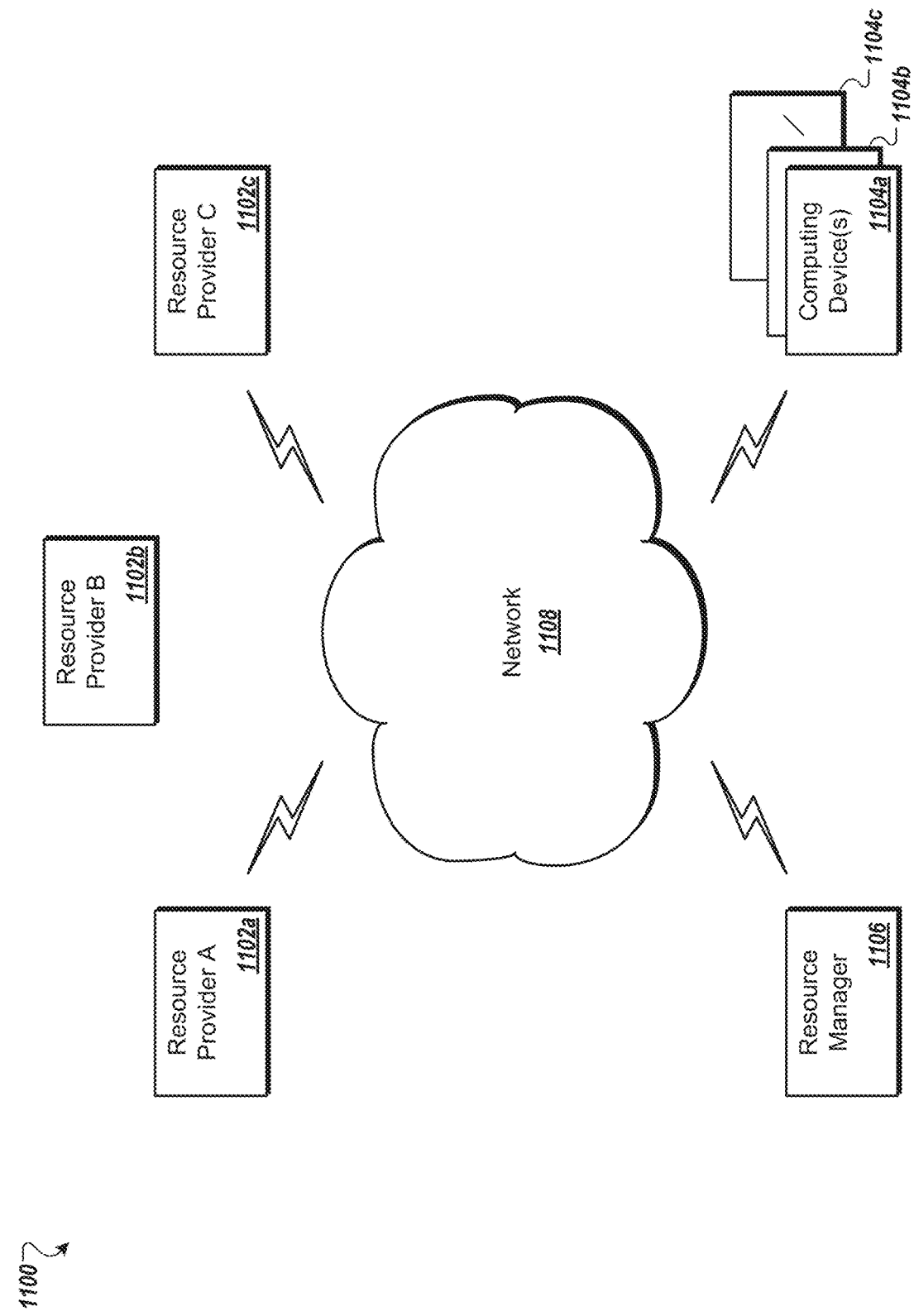
FIG. 11 shows a block diagram of an exemplary cloud computing environment.

As shown in FIG. 11, an implementation of a network environment 1100 for use in performing minimally invasive surgical techniques is shown and described. In brief overview, referring now to FIG. 11, a block diagram of an exemplary cloud computing environment 1100 is shown and described. The cloud computing environment 1100 may include one or more resource providers 1102*a*, 1102*b*, 1102*c* (collectively, 1102). Each resource provider 1102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1102 may be connected to any other resource provider 1102 in the cloud computing environment 1100. In some implementations, the resource providers 1102 may be connected over a computer network 1108. Each resource provider 1102 may be connected to one or more computing device 1104*a*, 1104*b*, 1104*c* (collectively, 1104), over the computer network 1108.

The cloud computing environment 1100 may include a resource manager 1106. The resource manager 1106 may be connected to the resource providers 1102 and the computing devices 1104 over the computer network 1108. In some implementations, the resource manager 1106 may facilitate the provision of computing resources by one or more resource providers 1102 to one or more computing devices 1104. The resource manager 1106 may receive a request for a computing resource from a particular computing device 1104. The resource manager 1106 may identify one or more resource providers 1102 capable of providing the computing resource requested by the computing device 1104. The resource manager 1106 may select a resource provider 1102 to provide the computing resource. The resource manager 1106 may facilitate a connection between the resource provider 1102 and a particular computing device 1104. In some implementations, the resource manager 1106 may establish a connection between a particular resource provider 1102 and a particular computing device 1104. In some implementations, the resource manager 1106 may redirect a particular computing device 1104 to a particular resource provider 1102 with the requested computing resource.

Figure 12:
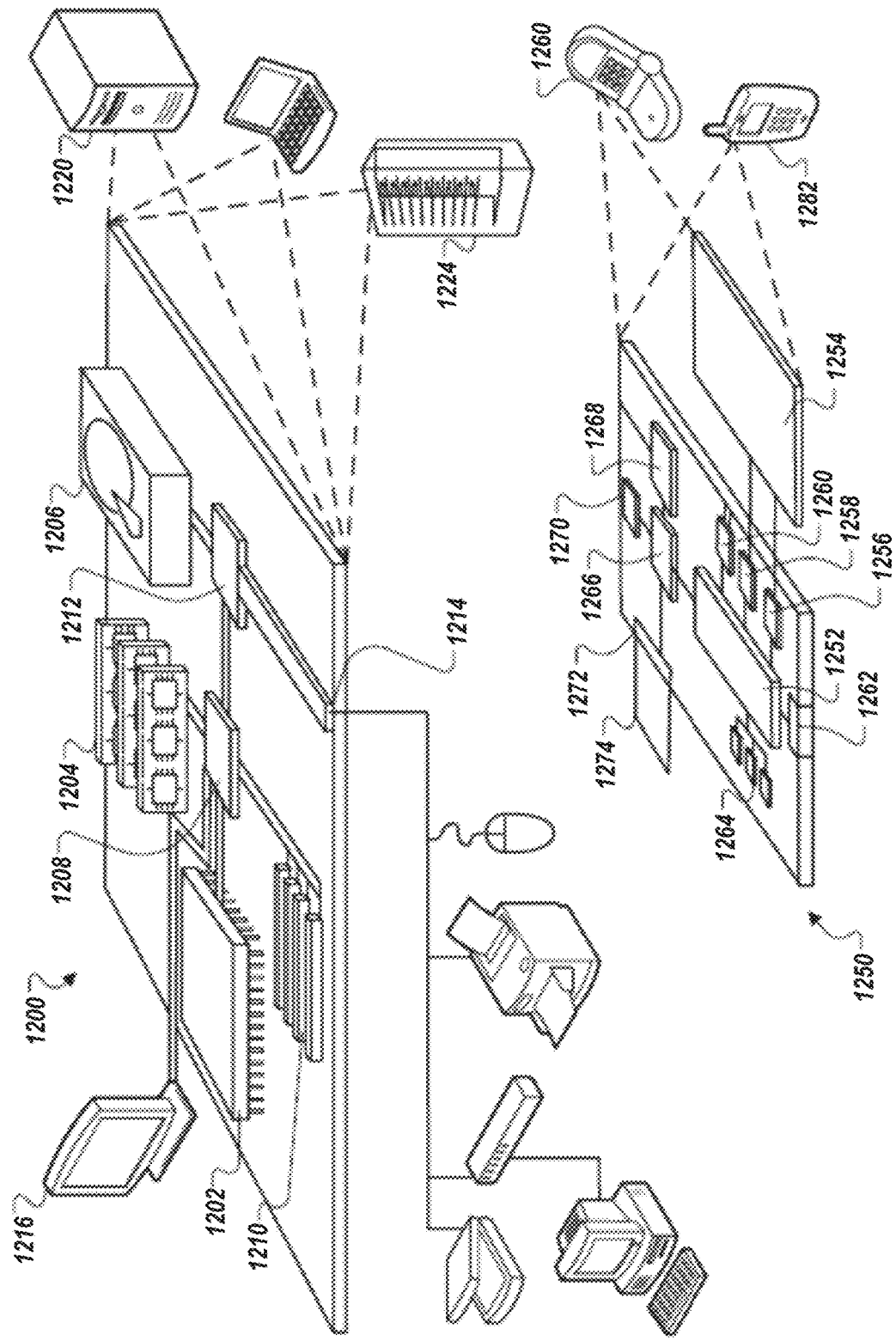
FIG. 12 is a block diagram of a computing device and a mobile computing device.

FIG. 12 shows an example of a computing device 1200 and a mobile computing device 1250 that can be used to implement the techniques described in this disclosure. The computing device 1200 is intended to represent various forms of digital computers, such as laptops, desktops, workstations, personal digital assistants, servers, blade servers, mainframes, and other appropriate computers. The mobile computing device 1250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1200 includes a processor 1202, a memory 1204, a storage device 1206, a high-speed interface 1208 connecting to the memory 1204 and multiple high-speed expansion ports 1210, and a low-speed interface 1212 connecting to a low-speed expansion port 1214 and the storage device 1206. Each of the processor 1202, the memory 1204, the storage device 1206, the high-speed interface 1208, the high-speed expansion ports 1210, and the low-speed interface 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as a display 1216 coupled to the high-speed interface 1208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1204 stores information within the computing device 1200. In some implementations, the memory 1204 is a volatile memory unit or units. In some implementations, the memory 1204 is a non-volatile memory unit or units. The memory 1204 may also be another form of computer-readable medium, such as a magnetic or optical disk.

The storage device 1206 is capable of providing mass storage for the computing device 1200. In some implementations, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1202), perform one or more methods, such as those described above. The instructions can also be stored by one or more storage devices such as computer- or machine-readable mediums (for example, the memory 1204, the storage device 1206, or memory on the processor 1202).

The high-speed interface 1208 manages bandwidth-intensive operations for the computing device 1200, while the low-speed interface 1212 manages lower bandwidth-intensive operations. Such allocation of functions is an example only. In some implementations, the high-speed interface 1208 is coupled to the memory 1204, the display 1216 (e.g., through a graphics processor or accelerator), and to the high-speed expansion ports 1210, which may accept various expansion cards (not shown). In the implementation, the low-speed interface 1212 is coupled to the storage device 1206 and the low-speed expansion port 1214. The low-speed expansion port 1214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. In addition, it may be implemented in a personal computer such as a laptop computer 1222. It may also be implemented as part of a rack server system 1224. Alternatively, components from the computing device 1200 may be combined with other components in a mobile device (not shown), such as a mobile computing device 1250. Each of such devices may contain one or more of the computing device 1200 and the mobile computing device 1250, and an entire system may be made up of multiple computing devices communicating with each other.

The mobile computing device 1250 includes a processor 1252, a memory 1264, an input/output device such as a display 1254, a communication interface 1266, and a transceiver 1268, among other components. The mobile computing device 1250 may also be provided with a storage device, such as a micro-drive or other device, to provide additional storage. Each of the processor 1252, the memory 1264, the display 1254, the communication interface 1266, and the transceiver 1268, are interconnected using various buses, and several of the components may be mounted on a common motherboard or in other manners as appropriate.

The processor 1252 can execute instructions within the mobile computing device 1250, including instructions stored in the memory 1264. The processor 1252 may be implemented as a chipset of chips that include separate and multiple analog and digital processors. The processor 1252 may provide, for example, for coordination of the other components of the mobile computing device 1250, such as control of user interfaces, applications run by the mobile computing device 1250, and wireless communication by the mobile computing device 1250.

The processor 1252 may communicate with a user through a control interface 1258 and a display interface 1256 coupled to the display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may provide communication with the processor 1252, so as to enable near area communication of the mobile computing device 1250 with other devices. The external interface 1262 may provide, for example, for wired communication in some implementations, or for wireless communication in other implementations, and multiple interfaces may also be used.

The memory 1264 stores information within the mobile computing device 1250. The memory 1264 can be implemented as one or more of a computer-readable medium or media, a volatile memory unit or units, or a non-volatile memory unit or units. An expansion memory 1274 may also be provided and connected to the mobile computing device 1250 through an expansion interface 1272, which may include, for example, a SIMM (Single In Line Memory Module) card interface. The expansion memory 1274 may provide extra storage space for the mobile computing device 1250, or may also store applications or other information for the mobile computing device 1250. Specifically, the expansion memory 1274 may include instructions to carry out or supplement the processes described above, and may include secure information also. Thus, for example, the expansion memory 1274 may be provided as a security module for the mobile computing device 1250, and may be programmed with instructions that permit secure use of the mobile computing device 1250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1252), perform one or more methods, such as those described above. The instructions can also be stored by one or more storage devices, such as one or more computer- or machine-readable mediums (for example, the memory 1264, the expansion memory 1274, or memory on the processor 1252). In some implementations, the instructions can be received in a propagated signal, for example, over the transceiver 1268 or the external interface 1262.

The mobile computing device 1250 may communicate wirelessly through the communication interface 1266, which may include digital signal processing circuitry where necessary. The communication interface 1266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1268 using a radio-frequency. In addition, short-range communication may occur, such as using a Bluetooth®, Wi-Fi™, or other such transceiver (not shown). In addition, a GPS (Global Positioning System) receiver module 1270 may provide additional navigation- and location-related wireless data to the mobile computing device 1250, which may be used as appropriate by applications running on the mobile computing device 1250.

The mobile computing device 1250 may also communicate audibly using an audio codec 1260, which may receive spoken information from a user and convert it to usable digital information. The audio codec 1260 may likewise generate audible sound for a user, such as through a speaker, e.g., in a handset of the mobile computing device 1250. Such sound may include sound from voice telephone calls, may include recorded sound (e.g., voice messages, music files, etc.) and may also include sound generated by applications operating on the mobile computing device 1250.

The mobile computing device 1250 may be implemented in a number of different forms, as shown in the figure. For example, it may be implemented as a cellular telephone 1280. It may also be implemented as part of a smart-phone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for performing minimally invasive surgical techniques are provided. Having described certain implementations of methods and apparatus for supporting minimally invasive surgical techniques, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A robotic surgical system for performing minimally invasive surgery, the system comprising:
 a robotic arm with an end effector;
 a first dilator to access a vertebrae of a patient through an incision of a patient, wherein the first dilator defines a working channel for accessing the vertebrae;
 one or more subsequent dilators sized and shaped to slide over the first dilator and/or one or more of the one or more subsequent dilators, wherein: the one or more subsequent dilators comprise a last added dilator having a distal end adapted to be inserted through the incision of the patient to enlarge the incision, each of the one or more subsequent dilators are configured to be positioned over the preceding dilators and increase the size of the working channel, each dilator except the last added dilator being configured to be removed from the patient thereby leaving the last added dilator,
 a dilator fixator adapted to be attached to the end effector, the last added dilator being configured to be attached to the dilator fixator; and
 a manipulator configured to allow robotically-assisted or unassisted positioning and/or movement of the end effector by a user with at least four degrees of freedom thereby automatically adjusting an angle and/or position of the attached last added dilator with respect to the vertebrae and aligning an axis defined by the last added dilator with a desired trajectory during a surgical procedure without removal of the last added dilator from the patient tissue during the repositioning, the manipulator further programmed to be automatically repositioned in response to the user changing the desired trajectory during the surgical procedure.

2. The system of claim 1, wherein each one or more subsequent dilators have a circumference larger than the circumference of the first dilator, and the one or more subsequent dilators increase the size of the working channel as each subsequent dilator is added.

3. The system of claim 1, comprising: a surgical instrument guide configured to be placed inside of the attached dilator, wherein the surgical instrument guide is sized and shaped to fit at least partially inside the attached dilator along an axis defined by the dilator.

4. The system of claim 3, wherein the end effector comprises the surgical instrument guide attached thereto, configured to hold and/or restrict movement of a surgical instrument therethrough.

5. The system of claim 4, wherein the surgical instrument guide is at least one of a drill bit guide, tap guide, screwdriver guide, screw guide, awl guide, and implant guide.

6. The system of claim 5, wherein the surgical instrument is at least one of a drill bit, tap, screwdriver, screw, implant, and awl, wherein the surgical instrument is configured to slide through the surgical instrument guide.

7. The system of claim 1, wherein the attached dilator is the dilator with largest circumference.

8. The system of claim 1, wherein the attached dilator is configured to hold and/or restrict movement of a surgical instrument therethrough.

9. The system of claim 1, wherein the manipulator comprises: a processor; and a memory, the memory storing instructions that, when executed by the processor, cause the processor to: store a transformation between the actual patient anatomy and one or more medical images; determine an ideal implant trajectory; and provide, for display on a graphical user interface, the ideal implant trajectory for review by the surgeon, wherein (i) the surgeon may adapt the ideal implant trajectory if needed using hands-on planning, and (ii) the surgeon acknowledges the ideal implant trajectory or the adapted trajectory thereby causing the acknowledged trajectory to be stored as the desired trajectory.

10. The system of claim 1, further comprising a tool guide tube adapted to be attached to the end effector at the same time as the last added dilator and sized to slidably guiding a surgical tool through the working channel formed by the last dilator.

* * * * *